(12) United States Patent
Dyllick-Brenzinger et al.

(10) Patent No.: US 8,263,327 B2
(45) Date of Patent: Sep. 11, 2012

(54) ENZYMATIC METHOD FOR THE PRODUCTION OF MICROCAPSULES

(75) Inventors: Rainer Dyllick-Brenzinger, Neustadt (DE); Yvonne Dieckmann, Hassloch (DE); Dietmar Haering, Neu-Edingen (DE); Bernhard Sturm, Ludwigshafen (DE); Michael Schroers, Ludwigshafen (DE); Harald Keller, Ludwigshafen (DE)

(73) Assignee: BASF SE, Ludwigshafen (DE)

( * ) Notice: Subject to any disclaimer, the term of this patent is extended or adjusted under 35 U.S.C. 154(b) by 267 days.

(21) Appl. No.: 12/597,074

(22) PCT Filed: Apr. 18, 2008

(86) PCT No.: PCT/EP2008/054702
§ 371 (c)(1),
(2), (4) Date: Oct. 22, 2009

(87) PCT Pub. No.: WO2008/132067
PCT Pub. Date: Nov. 6, 2008

(65) Prior Publication Data
US 2010/0120617 A1 May 13, 2010

(30) Foreign Application Priority Data
Apr. 26, 2007 (EP) .................................... 07107015

(51) Int. Cl.
*C12Q 1/00* (2006.01)
(52) U.S. Cl. .............................. 435/4; 424/490; 504/359
(58) Field of Classification Search ...... 435/4; 424/490; 504/359
See application file for complete search history.

(56) References Cited

U.S. PATENT DOCUMENTS

| 4,637,905 | A | | 1/1987 | Gardner |
| 5,780,389 | A | * | 7/1998 | Krause et al. ................ 504/359 |
| 6,022,500 | A | * | 2/2000 | John et al. ...................... 264/4.1 |
| 6,146,665 | A | | 11/2000 | Marchessault et al. |
| 6,849,591 | B1 | | 2/2005 | Boeckh et al. |
| 7,691,296 | B2 | | 4/2010 | Ju et al. |
| 2003/0194443 | A1 | * | 10/2003 | Yano et al. .................... 424/497 |
| 2007/0042184 | A1 | * | 2/2007 | Coyne et al. ................ 428/402.2 |
| 2008/0167418 | A1 | | 7/2008 | Kong et al. |
| 2008/0275182 | A1 | | 11/2008 | Kong et al. |
| 2009/0220789 | A1 | * | 9/2009 | DeSimone et al. ........... 428/402 |
| 2009/0318605 | A1 | | 12/2009 | Dyllick-Brenzinger et al. |
| 2010/0015676 | A1 | | 1/2010 | Kreitschmann et al. |
| 2010/0048655 | A1 | | 2/2010 | Koltzenburg et al. |
| 2010/0068525 | A1 | | 3/2010 | Jung et al. |
| 2010/0122379 | A1 | | 5/2010 | Dieckmann et al. |
| 2011/0230343 | A1 | | 9/2011 | Schroers et al. |

FOREIGN PATENT DOCUMENTS

| DE | 19932144 | 1/2001 |
| DE | 10 2005 007 374 | 8/2006 |
| EP | 1 275 378 | 1/2003 |
| EP | 1 421 990 | 5/2004 |
| WO | WO 02/069922 | 9/2002 |
| WO | WO 2004/035801 | 4/2004 |
| WO | WO 2004/105734 | 12/2004 |
| WO | WO 2006/010083 | 1/2006 |
| WO | WO 2006/058696 | 6/2006 |
| WO | WO 2006/058697 | 6/2006 |
| WO | WO 2008/025794 | 3/2008 |
| WO | WO 2008/034813 | 3/2008 |
| WO | WO 2008/040786 | 4/2008 |
| WO | WO 2008/064986 | 6/2008 |
| WO | WO 2008/064987 | 6/2008 |
| WO | WO 2008/064990 | 6/2008 |
| WO | WO 2008/065050 | 6/2008 |
| WO | WO 2008/071649 | 6/2008 |
| WO | WO 2010/046286 | 4/2010 |

OTHER PUBLICATIONS

Tiarks F. et al. The Controlled Generation of Nanosized Structures in Miniemulsions. Progress Colloid Polymer Science 117:110-112, 2001.*
Oh J. et al. Inverse Miniemulsion ATRP. JACS 128:5578-5584, 2006.*
Landfester K. Synthesis of Colloidal Particles in Miniemulsions. Annual Review Material Research. 36:231-279, 2006.*
International Search Report for International Application No. PCT/EP2008/054702.
International Preliminary Report on Patentability for International Application No. PCT/EP2008/054702.

* cited by examiner

*Primary Examiner* — Ralph Gitomer
(74) *Attorney, Agent, or Firm* — Brinks, Hofer, Gilson & Lione (57) ABSTRACT

The present invention provides a process for producing microcapsules. The microcapsules have an effect-substance-containing capsule core and a polymer-containing capsule covering. The capsule covering is formed by enzyme-catalyzed polymerization of monomers which are present in an inverse miniemulsion, as well as microcapsules and dispersions. The present invention also provides for using the microcapsules and microcapsule dispersions as components in colorants, cosmetics, pharmaceuticals, crop protection agents, fertilizers, and additives for foods or animal feed.

11 Claims, 3 Drawing Sheets

ENZYMATIC METHOD FOR THE PRODUCTION OF MICROCAPSULES

This application is a National Stage application of International Application No. PCT/EP2008/054702 filed Apr. 18, 2008, the entire contents of which is hereby incorporated herein by reference. This application also claims the benefit under 35 U.S.C. §119 of European Patent Application No. 07107015.5, filed Apr. 26, 2007, the entire contents of which is hereby incorporated herein by reference.

The present invention relates to a process for producing microcapsules comprising a polymer-containing capsule covering and an effect-substance-containing capsule core. It further relates to microcapsules and dispersions comprising microcapsules obtainable by the process according to the invention.

The invention further relates to the use of said microcapsules and dispersions comprising microcapsules as component in colorants, cosmetics, pharmaceuticals, crop protection agents, fertilizers, additives for foods or animal feed, auxiliaries for polymers, paper, textile, leather, coatings or detergents and cleaners.

Combinations of preferred features with other preferred features are encompassed by the present invention.

Microcapsules are known in a very wide variety of embodiments and are used for various purposes depending on the imperviousness of the capsule wall. For example, they serve to protect core materials which are only to be released through targeted mechanical destruction of the capsule covering, for example dye precursors for copy papers or encapsulated fragrances. In such fields of application, capsule covering materials based on gelatin, polyurethane resin, melamine formaldehyde resin and polyacrylate are known. Different requirements are placed on wall materials for plant or pharmaceutical active compounds than core materials for which what matters is a perviousness of the capsule covering which permits controlled release and targeted transportation of the active compounds. In this connection, besides the capsules produced by chemical processes, mechanicophysical preparation processes are also known.

Chemical or physical methods are generally known for producing microcapsules. In the case of physical methods, dissolved polymers are usually applied to the material to be encapsulated and converted to a solid capsule wall by physical methods, such as spray-drying or solvent extraction. In the case of chemical methods, the solid capsule wall is formed as a result of a chemical reaction, for example by polymerization of monomers, on the material to be encapsulated. An additional physical step for the formation of the solid microcapsule is not necessary.

Microcapsules comprising a polymer-containing capsule covering and an effect-substance-containing capsule core, and processes for their production, are generally known. Microcapsules of this type can be produced starting from polymeric feed materials for the capsule covering.

For example EP 1 421 990 relates to a process for producing microcapsules where a polyester, which is dispersed in a polyol, is emulsified with an enzyme as effect substance, which is dispersed in a polyol.

U.S. Pat. No. 4,637,905 relates to a process for producing microcapsules with 1 to 2000 μm, where a dispersion of polylactic acid with a protein as effect substance is prepared, some of the solvent is evaporated off and, finally, the concentrated dispersion is added to a third solvent for encapsulation of the effect substance.

WO 2002/069922 relates to microcapsules with an oxidoreductase-containing aqueous core and a polyester-containing covering. The production takes place by emulsifying an aqueous enzyme solution with a polyester dissolved in an organic solvent, followed by introducing the primary emulsion into an aqueous solvent and then the removal of the organic solvent.

EP 1 275 378 relates to a physical process for producing particulate constructs, where an emulsion of synthethase and alkyl-coenzyme A is prepared, then polymerized, and, finally, the particulate construct is produced by removing the solvents.

U.S. Pat. No. 6,022,500 relates to a physical process for producing polymeric microspheres, where firstly, in an emulsion of monomers, a polymeric microsphere is produced and isolated, which is then brought into contact with a substance solution such that the microsphere is thereby filled with this substance.

The use of enzymes for the polymerization of monomers in aqueous emulsion is generally known, for example from WO 2004/035801, WO 2006/058697 or WO 2006/058696. Here, in each case polymer particles with a massive polymer matrix are formed.

DE 102005007374 relates to nanoparticles of the core-shell type. The shell is defined as a polymer which is hydrophobic and biocompatible. The polymer is, for example, polyacrylate, polyepoxide, polyurethane or polyester. The core is defined as an active substance which is enclosed by the polymer of the shell. The preparation takes place by free-radical polymerization, polyaddition, polycondensation or enzymatic or anionic polymerization. Details of the processes or examples are not specified.

It was an object of the present invention to provide a novel process for producing microcapsules comprising a polymer-containing capsule covering and an effect-substance-containing capsule core. In particular, it was an object of the present invention to provide a process in which the polymer-containing capsule covering is composed essentially of monomers only during the encapsulation. It was a further aspect of the object to produce the polymer-containing capsule covering under mild reaction conditions, so that even sensitive effect substances can be encapsulated.

The object was achieved by a process for producing microcapsules comprising an effect-substance-containing capsule core and a polymer-containing capsule covering, comprising the formation of the capsule covering by means of enzyme-catalyzed polymerization of monomers which are present in an inverse miniemulsion.

By means of the process according to the invention, an ensemble of microcapsules is generally produced. The process according to the invention generally leads to identically or similarly shaped microcapsules. Microcapsules produced according to the invention can assume any desired shape. They are preferably essentially spherical, for example ideally spherical, in shape.

A microcapsule produced according to the invention comprises a capsule covering and a capsule core. According to the invention, the aim is also to obtain a microcapsule which comprises at least one capsule covering and at least one capsule core. Thus, a microcapsule can, for example, have one capsule core and two capsule coverings. Likewise, a microcapsule can, for example, have a plurality of capsule cores, for example two capsule cores which are next to one another or one within the other, and a capsule covering, for example two capsule coverings which are next to one another or one within the other. Preferably, a microcapsule comprises one capsule covering and one capsule core. The process according to the invention generally leads to identically or similarly composed microcapsules. Since the process according to the invention produces an ensemble of microcapsules, a few individual microcapsules can vary in their composition and, for example, comprise no capsule core enthalten.

The average diameter of the microcapsules (can be determined as number-average by light scattering of a 1% strength by weight aqueous dispersion of microcapsules, obtainable by diluting the microcapsules with water and if appropriate separating off an organic phase) can vary within a wide range. It is generally more than 0.1 µm, preferably more than 0.6 µm, particularly preferably more than 0.8 µm. The diameter is preferably in the range from 0.1 to 2000 µm, preferably from 0.6 to 1000 µm, in particular from 0.8 to 800 µm. A capsule diameter which is in the lower range is preferred when higher mechanical stability of the microcapsules is desired. A diameter in the higher range is preferred in order to pack as much capsule content as possible into little wall material.

The thickness of the capsule covering can vary within a wide range. It is generally from 0.1 to 90%, preferably from 0.5 to 20%, of the capsule radius (can be determined via light/electron microscopy or light scattering).

The surface of the microcapsules can have functional groups. It is preferably little functionalized, in particular unfunctionalized, in order to prevent covalent or ionic interactions during storage or use. If the surface is little functionalized, preferably less than 0.02 functional groups are located per $nm^2$ on the surface (can be determined for example by quantification of the functional groups by means of titration, by labeling with colored reagents, or, if the groups have electrical charges, by measuring the electrophoretic mobility or the $\zeta$ potential). According to the invention, functional groups on the surface are understood as meaning those which are introduced into the polymer surface in a targeted manner by special monomers. Terminal alcohol, acid or ester groups of the covering polymers are naturally excepted.

The capsule core comprises at least one effect substance. The effect substance is present here in the core usually in solid, dissolved, emulsified or dispersed form. In one preferred embodiment, the capsule core comprises at least one effect substance and at least one inert substance, which is preferably a liquid. Suitable inert substances are, for example, all compounds present in the process according to the invention: dispersants, polar and/or nonpolar liquids, water or the catalytically effective enzymes. In particular, the capsule core comprises at least one effect substance and at least one polar solvent. The capsule core can also comprise incompletely polymerized monomer. According to one preferred embodiment, the capsule core comprises at least one polar liquid which forms the disperse phase of the inverse miniemulsion.

According to the invention, in the process for producing the microcapsules, enzymes are used which catalyze the polymerization of the monomers which are present in an inverse miniemulsion, with formation of the capsule covering.

For the description of enzymes, the EC classes developed by the "Nomenclature Committee of the International Union of Biochemistry and Molecular Biology (NC-IUBMB)" are used.

Suitable enzymes are all enzyme classes, preferably hydrolases and oxidoreductases, particularly preferably hydrolases. Mixtures of different enzyme classes are also suitable.

Suitable hydrolases [EC 3.x.x.x] are, for example, esterases [EC 3.1.x.x], proteases [EC 3.4.x.x], hydrolases which react with C—N bonds other than peptide bonds [EC 3.5.x.x] or hydrolases which react with acid anhydrides [EC 3.6.x.x]. According to the invention, in particular carboxylesterases [EC 3.1.1.1], lipases [EC 3.1.1.3] or cutinases [EC-3.1.1.47] are advantageously used. Examples thereof are lipase from *Achromobacter* sp., *Aspergillus* sp., *Candida* sp., *Candida antarctica, Mucor* sp., *Penicilium* sp., *Geotricum* sp., *Rhizopus* sp., *Burkholderia* sp., *Pseudomonas* sp., *Pseudomonas cepacia, Thermomyces* sp., porcine pancreas or wheatgerms and also carboxylesterases from *Bacillus* sp., *Pseudomonas* sp., *Burkholderia* sp., *Mucor* sp., *Saccharomyces* sp., *Rhizopus* sp., *Thermoanaerobium* sp., porcine liver or equine liver.

It is of course possible to use a single hydrolase or a mixture of different hydrolases. It is also possible to use the hydrolases in free and/or immobilized form. Preference is given to using lipase from *Pseudomonas cepacia, Burkholderia platarii* or *Candida antarctica* type B in free or immobilized form (for example Novozym® 435 from Novozymes A/S, Denmark).

Suitable oxidoreductases [EC 1.x.x.x] are preferably peroxidases [EC 1.11.1.x] and laccases [EC 1.10.3.2] in free or immobilized form. Enzyme-specific auxiliaries such as iron salts, acetylacetone or hydrogen peroxide are generally known to the person skilled in the art.

The total amount of the enzymes used is generally from 0.001 to 40% by weight, frequently from 0.1 to 15% by weight and often from 0.5 to 10% by weight, in each case based on the total amount of monomers. The amount depends on the purity of the enzyme used. Technical-grade or immobilized enzymes are generally used in higher amounts than purified enzymes. The person skilled in the art will also tailor the amount of catalyst according to how rapidly the reaction is to proceed.

Enzyme-catalyzed polymerizations of monomers are generally known, for example from Kobayashi et al., Chem. Rev 2001, 101, 3793-3818. For this, the person skilled in the art selects an enzyme which catalyzes the polymerization depending on the type of monomer. Oxidoreductases catalyze, for example, the polymerization of phenols, anilines or vinylic monomers. Hydrolases catalyze, for example, the polymerization of diols with diacids and diesters, of diamines with diacids or diesters, of lactones or of carbonates.

The use of an enzyme-catalyzed polymerization can take place in the presence of other compounds which catalyze the polymerization. The use of an enzyme-catalyzed polymerization can also take place before or after nonenzymatically catalyzed polymerization.

Suitable monomers for the reaction with hydrolases are hydroxycarboxylic acid compounds, dialcohol compounds or diacid compounds, particularly hydroxycarboxylic acid compounds. A combination of the upper monomers is likewise possible, with the combination of dialcohol compounds and diacid compounds being preferred.

In one preferred embodiment, the monomers are combined with a starter monomer which is a hydroxycarboxylic acid compound, dialcohol compound or a diacid compound. Preferably, the starter monomer is a dialcohol compound as described below, particularly ethylene glycol, 1,4-butanediol, glycerol, sorbitol, monosaccharide, disaccharide, polysaccharide or hydroxy-functional, dendritic polyester based on 2,2-dimethylolpropionic acid (Boltorn® grades, commercially available from Perstorp).

Hydroxycarboxylic acid compounds which may be used are the free hydroxycarboxylic acids with at least one free alcohol group and at least one free carboxylic acid group, their $C_1$-$C_5$-alkyl esters and/or their lactones. By way of example, mention may be made of glycolic acid, D-, L-, D,L-lactic acid, 6-hydroxyhexanoic acid (6-hydroxycaproic acid), 3-hydroxybutyric acid, 3-hydroxyvaleric acid, 3-hydroxycaproic acid, cyclic derivatives thereof, such as glycolide (1,4-dioxane-2,5-dione), D-, L-, D,L-dilactide (3,6-dimethyl-1,4-dioxane-2,5-dione), ε-caprolactone, β-butyrolactone, γ-butyrolactone, ω-dodecanolide (oxacyclotridecan-2-one), ω-undecanolide (oxacyclododecan-2-one) or ω-pentadecanolide (oxacyclohexadecan-2-one).

Suitable lactones are also bis- or tris-lactones which comprise two or three lactone groups, respectively. For example, (2,2'-bis(ε-caprolactone-4-yl)propane can be used. Bis-lactones can, for example, be synthesized according to Palmgren et al., Journal of Polymer Science A, 1997, 35, 1635-1649.

Likewise suitable are the esters of carbonic acid (carbonates), particularly linear and cyclic aliphatic carbonates, preferably $C_1$ to $C_8$-alkyl esters of carbonic acid, in particular trimethylene carbonate. Carbonates which do not react with the respective enzyme, for example propylene carbonate, are not suitable as monomer. Hydroxycarboxylic acid compounds which can be used are also the thiocarboxylic acid analogous to the aforementioned hydroxycarboxylic acid compounds, and its esters and thiolactones.

It is of course also possible to use mixtures of different hydroxycarboxylic acid compounds.

Preferred hydroxycarboxylic acid compounds are lactones, in particular $C_2$ to $C_{18}$-alkylene lactones, very particularly preferably ε-caprolactone.

Dicarboxylic acid compounds which can be used are in principle all $C_2$-$C_{40}$-aliphatic, $C_3$-$C_{20}$-cycloaliphatic, aromatic or heteroaromatic compounds which have at least two carboxylic acid groups (carboxy groups; —COOH) or derivatives thereof. The derivatives used are in particular $C_1$-$C_{10}$-alkyl, preferably methyl, ethyl, n-propyl or isopropyl, mono- or diesters of the aforementioned dicarboxylic acids, and also the corresponding dicarboxylic acid anhydrides.

Examples of dicarboxylic acid compounds are ethanedioic acid (oxalic acid), propanedioic acid (malonic acid), butanedioic acid (succinic acid), pentanedioic acid (glutaric acid), hexanedioic acid (adipic acid), heptanedioic acid (pimelic acid), octanedioic acid (suberic acid), nonanedioic acid (azelaic acid), decanedioic acid (sebacic acid), undecanedioic acid, dodecanedioic acid, tridecanedioic acid (brassylic acid), $C_{32}$-dimer fatty acid benzene-1,2-dicarboxylic acid (phthalic acid), benzene-1,3-dicarboxylic acid (isophthalic acid) or benzene-1,4-dicarboxylic acid (terephthalic acid), methyl esters thereof, for example dimethyl ethanedioate, dimethyl propanedioate, dimethyl butanedioate, dimethyl pentanedioate, dimethyl hexanedioate, dimethyl heptanedioate, dimethyl octanedioate, dimethyl nonanedioate, dimethyl decanedioate, dimethyl undecanedioate, dimethyl dodecanedioate, dimethyl tridecanedioate, $C_{32}$-dimer fatty acid dimethyl ester, dimethyl phthalate, dimethyl isophthalate or dimethyl terephthalate, and also anhydrides thereof, for example butanedicarboxylic anhydride, pentanedicarboxylic anhydride or phthalic anhydride. It is of course also possible to use mixtures of the aforementioned dicarboxylic acid compounds. Oligoesters and polyesters with at least two free carboxy groups, in particular carboxy-terminated oligo- and polyesters, can likewise be used as dicarboxylic acid component.

Likewise, the esters of polycarboxylic acids, such as, for example, citric acid and butanetetracarboxylic acid, can also be used.

Preference is given to using the free dicarboxylic acids, particularly $C_4$ to $C_{36}$ aliphatic dicarboxylic acids, in particular butanedioic acid, hexanedioic acid, decanedioic acid, dodecanedioic acid and their corresponding dimethyl and diethyl esters.

Diol compounds which can be used are branched or linear alkanes having 2 to 18 carbon atoms, preferably 4 to 14 carbon atoms, cycloalkanes having 5 to 20 carbon atoms or aromatic compounds which comprise at least two alcohol groups. Examples of suitable alkanedials are ethylene glycol, 1,2-propanediol, 1,3-propanediol, 1,2-butanediol, 1,4-butanediol, 1,5-pentanediol, 1,6-hexanediol, 1,7-heptanediol, 1,8-octanediol, 1,9-nonanediol, 1,10-decanediol, 1,11-undecanediol, 1,12-dodecanediol, 1,13-tridecanediol, 2,4-dimethyl-2-ethyl-1,3-hexanediol, 2,2-dimethyl-1,3-propanediol (neopentyl glycol), 2-ethyl-2-butyl-1,3-propanediol, 2-ethyl-2-isobutyl-1,3-propanediol or 2,2,4-trimethyl-1,6-hexanediol. Of particular suitability are ethylene glycol, 1,3-propanediol, 1,4-butanediol and 2,2-dimethyl-1,3-propanediol, 1,6-hexanediol or 1,12-dodecanediol.

Examples of cycloalkanediols are 1,2-cyclopentanediol, 1,3-cyclopentanediol, 1,2-cyclohexanediol, 1,3-cyclohexanediol, 1,4-cyclohexanediol, 1,2-cyclohexanedimethanol (1,2-dimethylolcyclohexane), 1,3-cyclohexanedimethanol (1,3-dimethylolcyclohexane), 1,4-cyclohexanedimethanol (1,4-dimethylolcyclohexane) or 2,2,4,4-tetramethyl-1,3-cyclobutanediol.

Examples of suitable aromatic diols are 1,4-dihydroxybenzene, 1,3-dihydroxybenzene, 1,2-dihydroxybenzene, bisphenol A (2,2-bis(4-hydroxyphenyl)propane), 1,3-dihydroxynaphthalene, 1,5-dihydroxynaphthalene or 1,7-dihydroxynaphthalene. Diol compounds which can be used are, however, also polyetherdiols, for example diethylene glycol, triethylene glycol, polyethylene glycol (with more than 4 ethylene oxide units), propylene glycol, dipropylene glycol, tripropylene glycol, polypropylene glycol (with more than 4 propylene oxide units) and polytetrahydrofuran (poly-THF), in particular diethylene glycol, triethylene glycol and polyethylene glycol (with more than 4 ethylene oxide units). Compounds whose number-average molecular weight (Mn) is generally in the range from 200 to 10 000, preferably from 600 to 5000 g/mol, are used as poly-THF, polyethylene glycol or polypropylene glycol.

Oligoesters and polyesters with at least two free alcohol groups, preferably dihydroxy-terminated oligo- and polyesters, are likewise suitable.

Further examples of suitable diol compounds with more than two alcohol groups are glycerol, sorbitol, trimethylolpropane, pentaerythritol, monosaccharides such as fructose, glycose or mannose, disaccharides such as sucrose, oligosaccharides and also substitution products thereof, or cellulose derivatives such as acetates.

Diol compounds which can be used are also a dithiol analogous to the aforementioned diol compounds.

It is of course also possible to use mixtures of the aforementioned diol compounds or dithiols.

Preference is given to aliphatic alkanediols and polyetherdiols, particularly preferably linear and branched aliphatic alkanediols having 2 to 18 carbon atoms, in particular ethylene glycol, 1,4-butanediol, 1,6-hexanediol, sorbitol and neopentyl glycol.

The monomers described above can produce linear, branched or crosslinked polyesters, depending on whether difunctional monomers or more highly functional monomers are used.

Suitable monomers for the reaction with oxidoreductases are phenols, anilines and vinylic monomers. Suitable phenols are phenols and mono- and polysubstituted phenol. Substituents may be, for example, halogen, $C_1$-$C_{18}$-alkyl, mono- or polynuclear aryl or amine. Suitable anilines are aniline and mono- and polysubstituted anilines. Substituents may be, for example, halogen, $C_1$-$C_{18}$-alkyl, mono- or polynuclear aryl or hydroxy. Suitable vinylic monomers are compounds with at least one nonaromatic double bond. Examples are (meth) acrylic acid and its $C_1$ to $C_{30}$-aliphatic alkyl esters, itaconic acid and its $C_1$ to $C_{30}$-aliphatic alkyl esters, or styrenes. Suitable styrenes are styrene and mono- and polysubstituted styrenes. Substituents may be, for example, halogen, $C_1$-$C_{18}$-alkyl, mono- or polynuclear aryl, amine or hydroxy.

Preference is given to vinylic monomers, in particular (meth)acrylic acid and its $C_1$ to $C_{30}$-aliphatic alkyl esters or styrene.

The monomers are generally present in the reaction mixture to 0.1 to 20% by weight, preferably to 0.5 to 10% by weight, in particular to 1 to 5% by weight, based on the total mixture. In a preferred embodiment, at least one lactone is present to 0.1 to 20% by weight, preferably to 0.5 to 10% by weight, in particular to 1 to 5% by weight, based on the total mixture.

According to the process according to the invention, dispersants can be used. These may in principle be protective colloids, emulsifiers or mixtures thereof. In this connection, it goes without saying that the emulsifiers and/or protective colloids are selected such that they are compatible in particular with the enzymes used and do not deactivate them.

The polymerization can be carried out in the presence of protective colloids, if appropriate also in addition to emulsifiers. They generally have average molar masses Mw of above 500, preferably of more than 1000 g/mol. Examples of protective colloids are polyvinyl alcohols, cellulose derivatives such as carboxymethylcellulose, polyvinylpyrrolidone, polyethylene glycols, graft polymers of vinyl acetate and/or vinyl propionate onto polyethylene glycols, polyethylene glycols terminally capped at one or both ends with alkyl, carboxyl or amino groups, polydiallyldimethylammonium chlorides and/or polysaccharides such as, in particular, water-soluble starches or starch derivatives.

Often, the dispersants used are exclusively emulsifiers. In general, emulsifiers are used whose relative molecular weights are, in contrast to the protective colloids, usually below 1000 g/mol. They may be either of anionic, cationic or nonanionic nature. When using mixtures of interface-active substances, the individual components must of course be compatible with one another, something which can be checked if in doubt by means of a few exploratory experiments. In general, anionic emulsifiers are compatible with one another and with nonionic emulsifiers. The same is also true for cationic emulsifiers, whereas anionic and cationic emulsifiers are in most cases not compatible with one another.

The polymerization can, if appropriate, also be carried out in the presence of finely divided, water-insoluble inorganic emulsifiers (so-called Pickering emulsifiers), for example barium sulfate.

Customary nonionic emulsifiers are, for example, ethoxylated mono-, di- and trialkylphenols (degree of ethoxylation from 3 to 50, alkyl radial: $C_4$ to $C_{12}$) and also ethoxylated fatty alcohols (degree of ethoxylation from 3 to 80; alkyl radial: $C_8$ to $C_{36}$). Examples thereof are the Lutensol® A brands ($C_{12}$ to $C_{14}$-fatty alcohol ethoxylates, degree of ethoxylation from 3 to 8), Lutensol® AO brands ($C_{13}$ to $C_{15}$-oxo alcohol ethoxylates, degree of ethoxylation from 3 to 30), Lutensol® AT brands ($C_{16}$ to $C_{18}$-fatty alcohol ethoxylates, degree of ethoxylation from 11 to 80), Lutensol® ON brands (C10-oxo alcohol ethoxylates, degree of ethoxylation from 3 to 11) and the Lutensol® TO brands (C13-oxo alcohol ethoxylates, degree of ethoxylation from 3 to 20) from BASF SE.

Customary anionic emulsifiers are, for example, alkali metal and ammonium salts of alkyl sulfates (alkyl radial: C8 to C12), of sulfuric acid half-esters of ethoxylated alkanols (degree of ethoxylation from 4 to 30, alkyl radial: $C_{12}$ to $C_{18}$) and ethoxylated alkylphenols (degree of ethoxylation from 3 to 50, alkyl radial: $C_4$ to $C_{12}$), of alkylsulfonic acids (alkyl radial: $C_{12}$ to $C_{18}$) and of alkylarylsulfonic acids (alkyl radial: $C_9$ to $C_{18}$).

Further anionic emulsifiers which have proven useful are also compounds of the general formula (I)

in which $R^1$ and $R^2$ are H atoms or $C_4$- to $C_{24}$-alkyl and are not simultaneously H atoms, and $M^1$ and $M^2$ may be alkali metal ions and/or ammonium ions. In the general formula (I), $R^1$ and $R^2$ are preferably linear or branched alkyl radicals having 6 to 18 carbon atoms, in particular having 6, 12 and 16 carbon atoms or hydrogen, where $R^1$ and $R^2$ are not both simultaneously H atoms. $M^1$ and $M^2$ are preferably sodium, potassium or ammonium, where sodium is particularly preferred. Compounds (I) in which $M^1$ and $M^2$ are sodium, $R^1$ is a branched alkyl radial having 12 carbon atoms and $R^2$ is an H atom or $R^1$ are particularly advantageous. Technical-grade mixtures which have a fraction of from 50 to 90% by weight of the monoalkylated product, such as, for example, Dowfax® 2A1 (brand from Dow Chemical Company) are often used. Suitable cationic emulsifiers are generally cationic salts having a $C_6$- to $C_{18}$-alkyl-, -alkylaryl or heterocyclic radical, for example primary, secondary, tertiary or quaternary ammonium salts, alkanolammonium salts, pyridinium salts, imidazolinium salts, oxazolinium salts, morpholinium salts, thiazolinium salts, and salts of amine oxides, quinolinium salts, isoquinolinium salts, tropylium salts, sulfonium salts and phosphonium salts. By way of example, mention may be made of dodecylammonium acetate or the corresponding sulfate, the sulfates or acetates of the various 2-(N,N,N-trimethylammonium)ethylparaffinic acid esters, N-cetylpyridinium sulfate, N-lauryl-pyridinium sulfate, and also N-cetyl-N,N,N-trimethylammonium sulfate, N-dodecyl-N,N,N-trimethylammonium sulfate, N-octyl-N,N,N-trimethylammonium sulfate, N,N-distearyl-N,N-dimethylammonium sulfate, and also the Gemini surfactant N,N'-(lauryldimethyl) ethylenediamine disulfate, ethoxylated tallow fatty alkyl-N-methylammonium sulfate and ethoxylated oleylamine (for example Uniperol® AC from BASF Aktiengesellschaft, ca. 12 ethylene oxide units). It is essential that the anionic counter groups are as little nucleophilic as possible, such as, for example, perchlorate, sulfate, phosphate, nitrate and carboxylates, such as acetate, trifluoroacetate, trichioroacetate, propionate, oxalate, citrate, benzoate, and also conjugated anions of organosulfonic acids, such as, for example, methylsulfonate, trifluoromethylsulfonate and paratoluenesulfonate, also tetrafluoroborate, tetraphenylborate, tetrakis (pentafluorophenyl)borate, tetrakis[bis(3,5-trifluoromethyl)phenyl]borate, hexafluorophosphate, hexafluoroarsenate or hexafluoroantimonate.

Preferred emulsifiers are nonionic emulsifiers, in particular ethoxylated alcohols and sorbitan ester, particularly preferably ethoxylated fatty alcohols and sorbitan fatty acid esters. Very particularly preferred mixtures comprise ethoxylated alcohols and sorbitan esters. In one preferred embodiment, the mixtures comprise ethoxylated alcohols and sorbitan esters.

In a further preferred embodiment, a polymer based on the end reaction product of polyisobutylene and maleic anhydride (PIBSA) and di(alkyl)ethanolamine is suitable. In a further preferred embodiment, block copolymers are suitable, as are described in Macromolecules 38 (16), 6882-6887, block copolymers based on isoprene and methyl methacrylate, as are described in WO 2008/009424, or poly((ethylene-co-butylene)-block-ethylene oxide).

The emulsifiers preferably used as dispersants are advantageously used in a total amount of from 0.005 to 20% by weight, preferably 0.01 to 15% by weight, in particular 0.1 to 10% by weight, in each case based on the total mixture.

The total amount of the protective colloids used as dispersants in addition to or instead of the emulsifiers is often 0.1 to 10% by weight and frequently 0.2 to 7% by weight, in each case based on the total mixture.

The inverse miniemulsion according to the invention in which the monomers are present comprises a continuous nonpolar phase and a discontinuous polar phase. The polar phase comprises a polar liquid and the nonpolar phase comprises a nonpolar liquid.

The effect substance is essentially present in the discontinuous phase in solid, dissolved, emulsified or dispersed form. The monomers, dispersants or enzymes can be present in distributed form either only in one of the two phases, or else in both phases, or at the interface of the two phases. In one preferred embodiment, the monomer is present to at least 50% by weight, preferably at least 60% by weight and in particular at least 80% by weight, in the polar phase.

In a further preferred embodiment, the polar liquid consists of at least one monomer and at least one effect substance.

The average size of the droplets of the discontinuous phase of the inverse miniemulsion according to the invention can preferably be determined by the principle of quasielastic dynamic light scattering on a 1% strength by weight miniemulsion, obtainable by diluting the inverse miniemulsion with the corresponding continuous phase and, if appropriate, separating off an organic phase (the so-called number-average droplet diameter $d_z$ of the unimodal analysis of the autocorrelation function). Further determination methods are light or electron microscopy, and also field flow fractionation. According to the invention, values for $d_z$ ascertained in such a way for the inverse miniemulsions are normally below 10 000 nm, often below 1000 nm, in most cases below 500 nm. According to the invention, the $d_z$ range from 2000 nm to 1000 nm is favorable. Normally, $d_z$ of the inverse miniemulsion to be used according to the invention is above 40 nm.

Suitable polar liquids are those whose solubility in the continuous nonpolar phase under reaction conditions is below 40% by weight, preferably below 10% by weight and in particular below 1% by weight (in each case based on the total amount of the continuous phase), such that a separate discontinuous polar phase is present. In one preferred embodiment, the polar liquid dissolves, at 20° C., the polymer of the capsule covering at most to 10% by weight, preferably at most to 3% by weight and particularly at most to 0.5% by weight, in each case based on the total mass of the polymer.

Suitable polar liquids are, for example, monools, such as $C_3$-$C_6$-alkanols, in particular tert-butanol and tert-amyl alcohol, pyridine, poly-$C_1$-$C_4$-alkylene glycol di-$C_1$-$C_4$-alkyl ethers, in particular polyethylene glycol di-$C_1$-$C_4$-alkyl ethers, such as, for example, dimethoxyethane, diethylene glycol dimethyl ether, polyethylene glycol dimethyl ether 500, $C_2$-$C_4$-alkylene carbonates, in particular propylene carbonate, $C_3$-$C_6$-alkyl acetic acid esters, in particular tert-butyl acetate, acetone, 1,4-dioxane, 1,3-dioxolane, tetrahydrofuran, dimethoxymethane, dimethoxyethane, aqueous buffers or water. It is of course also possible to use mixtures of the aforementioned solvents. Suitable polar liquids are also the aforementioned monomers or mixtures thereof.

The polar liquid can, for example, also comprise the effect substance used, or it can consist of it. Preferred polar liquid is propylene carbonate and mixtures containing propylene carbonate.

In one preferred embodiment, the polar liquid is the monomer or the monomers.

If the monomer used is a lactone, the polar liquid comprises less than 5% by weight, preferably less than 1% by weight and in particular less than 0.1% by weight, of water. If the polar liquid comprises water, it is advantageous if the aqueous reaction medium at room temperature (20 to 25° C.) has a pH of from 2 to 11, frequently from 3 to 9 and often from 6 to 8. In particular, in the aqueous reaction medium, a pH is established at which the enzyme has high catalytic activity and long service life. The appropriate measures for adjusting the pH, i.e. addition of corresponding amounts of acid, for example sulfuric acid, bases, for example aqueous solutions of alkali metal hydroxides, in particular sodium hydroxide or potassium hydroxide, or buffer substances, for example potassium dihydrogenphosphate/disodium hydrogenphosphate, acetic acid/sodium acetate, ammonium hydroxide/ammonium chloride, potassium dihydrogenphosphate/sodium hydroxide, borax/hydrochloric acid, borax/sodium hydroxide or tris(hydroxymethyl)aminomethane/hydrochloric acid are familiar to the person skilled in the art.

In order to further increase the polarity of the polar phase, it can additionally comprise so-called hydrophilic agents. Suitable hydrophilic agents are, for example, organic or inorganic salts or uncharged, very polar compounds. Examples of inorganic salts are sodium nitrite, sodium chloride, potassium chloride, lithium chloride, rubidium chloride. Examples of organic salts are trialkylammonium salts, ionic liquids, such as ethyl-methylimidazolium salts, or oligomers with stoichiometric fractions of anionic and cationic groups in the main chain or side chain. Preference is given to hydrophilic agents which do not reduce the catalytic activity of the enzymes.

Suitable nonpolar liquids are those whose solubility in the discontinuous polar phase under reaction conditions is below 10% by weight, preferably below 1% by weight and in particular below 0.1% by weight (in each case based on the total amount of the continuous phase), so that a separate continuous polar phase is present.

Suitable nonpolar liquids are, for example, liquid aliphatic or aromatic hydrocarbons having 5 to 30 carbon atoms, for example n-pentane and isomers, cyclopentane, n-hexane and isomers, cyclohexane, n-heptane and isomers, n-octane and isomers, n-nonane and isomers, n-decane and isomers, n-dodecane and isomers, n-tetradecane and isomers, n-hexadecane and isomers, n-octadecane and isomers, benzene, toluene, ethylbenzene, cumene, o-, m- or p-xylene, mesitylene.

Of suitability are also hydrocarbon mixtures in the boiling range from 30 to 250° C., such as partly hydrogenated mineral oil distillates (e.g. Isopar® brands, Exxon Mobil). Also suitable are olefins, for example isopolybutylenes or C6 to C30 alpha-olefins. It is likewise possible to use hydroxy compounds, such as saturated and unsaturated fatty alcohols having 10 to 28 carbon atoms, for example n-dodecanol, n-tetradecanol, n-hexadecanol and isomers thereof or cetyl alcohol, esters, such as, for example, fatty acid esters having 10 to 28 carbon atoms in the acid moiety and 1 to 10 carbon atoms in the alcohol moiety or esters of carboxylic acids and fatty alcohols having 1 to 10 carbon atoms in the carboxylic acid moiety and 10 to 28 carbon atoms in the alcohol moiety. Further suitable nonpolar liquids are paraffin oil (linear hydrocarbon mixture), silicone oil (polysiloxane), perfluorinated hydrocarbons, fluorosilicone oil, perfluorinated polyethers, fluorosilane or siloxanes, such as dimethylsiloxane.

Preferred nonpolar liquids are liquid aliphatic and aromatic hydrocarbons having 5 to 30 carbon atoms, in particular partly hydrogenated mineral oil distillates. In a further embodiment, nonpolar liquids are paraffin oil.

It is of course also possible to use mixtures of the aforementioned solvents.

The total amount of polar and nonpolar liquids is selected such that the total mixture reaches 100% by weight. It is generally from 10 to 90% by weight, preferably from 40 to 70% by weight, based on the total mixture.

The quantitative ratio of polar to nonpolar liquid is selected here such that a discontinuous phase is formed which essentially comprises the polar liquid. In one preferred embodiment, 20 to 80% by weight, preferably 40 to 70% by weight, of nonpolar liquid are used, in each case based on the total mixture. In a further preferred embodiment, 20 to 80% by weight, preferably 30 to 60% by weight, of polar liquid are used, in each case based on the total mixture. In a further preferred embodiment, 20 to 80% by weight, preferably 35 to 55% by weight, of hydrocarbon mixtures and 20 to 70% by weight, preferably 30 bis 60% by weight, of propylene carbonate are used, in each case based on the total mixture. Here, it must be ensured that the miniemulsions do not suffer a phase inversion, i.e. that the hydrophobic continuous phase does not turn into the disperse phase.

Within the context of the invention, effect substances are to be understood as meaning substances which, in commercial use of the product according to the invention, bring about effects desired by the user.

Effect substances are, for example, colorants, cosmetics, pharmaceuticals, crop protection agents, fertilizers, additives for foods or animal feed, auxiliaries for polymers, paper, textile, leather or detergents and cleaners.

Examples of colorants are dyes, printing inks, pigments, UV absorbers, optical brighteners or IR dyes. Whereas organic dyes have an absorption maximum in the wavelength range from 400 to 850 nm, optical brighteners have one or more absorption maxima in the range from 250 to 400 nm. As is known, optical brighteners, upon irradiation with UV light, emit a fluorescent beam in the visible range. Examples of optical brighteners are compounds from the classes of bis-styrylbenzenes, stilbenes, benzoxazoles, coumarins, pyrenes and naphthalenes. Also suitable are markers for liquids, for example mineral oil markers. In general, UV absorbers are understood as meaning compounds absorbing UV rays which deactivate the absorbed radiation in a nonradiative manner. Such compounds are used, for example, in sunscreen compositions and for stabilizing organic polymers.

Further suitable effect substances are cosmetics. Cosmetics are substances or preparations of substances which are solely or predominantly intended to be applied externally to the body of a person or his/her oral cavity for cleaning, care, protection, maintaining a good condition, perfuming, changing the appearance or for influencing body odor. Also suitable are, for example, insect repellents, such as icaridin or N,N-diethyl-meta-toluamide (DEET).

Moreover, all pharmaceuticals can be used as effect substances.

Crop protection agents and fertilizers can also be used as effective substances. Suitable crop protection agents are acaricides, algicides, aphicides, bactericides, fungicides, herbicides, insecticides, molluscicides, nematicides, germination inhibitors, safeners or growth regulators. Fungicides are compounds which kill fungi and their spores or inhibit their growth. Insecticides are compounds whose effect is targeted particularly against insects and their developmental forms. Herbicides are understood as meaning compounds which are active against generally all wild and cultivated plants which are undesired at their particular location (harmful plants). Examples of fertilizers are mineral single- or multinutrient fertilizers, organic and organic-mineral fertilizers or fertilizers with trace nutrients.

In a preferred embodiment, the effect substances are crop protection agents or mixtures of crop protection agents. In a further preferred embodiment, the crop protection agents are preferably herbicides, insecticides or fungicides.

The following list of crop protection agents shows possible active compounds, but is not intended to be limited to these.

The fungicide is selected from:

A) Strobilurins:
azoxystrobin, dimoxystrobin, enestroburin, fluoxastrobin, kresoxim-methyl, metominostrobin, orysastrobin, picoxystrobin, pyraclostrobin, pyribencarb, trifloxystrobin, 2-(2-(6-(3-chloro-2-methylphenoxy)-5-fluoropyrimidin-4-yloxy)phenyl)-2-methoxyimino-N-methylacetamide, 2-(ortho(2,5-dimethylphenyloxymethylene)-phenyl)-3-methoxyacrylic acid methyl ester, 3-methoxy-2-(2-(N-(4-methoxyphenyl-cyclopropanecarboximidoylsulfanylmethyl)phenyl) acrylic acid methyl ester, 2-(2-(3-(2,6-dichlorophenyl)-1-methylallylideneaminooxymethyl)phenyl)-2-methoxyimino-N-methylacetamide;

B) Carboxamides:
carboxanilides: benalaxyl, benalaxyl-M, benodanil, bixafen, boscalid, carboxin, fenfuram, fenhexamid, flutolanil, furametpyr, isopyrazam, isotianil, kiralaxyl, mepronil, metalaxyl, metalaxyl-M, ofurace, oxadixyl, oxycarboxin, penthiopyrad, tecloftalam, thifluzamide, tiadinil, 2-amino-4-methylthiazole-5-carboxanilide, 2-chloro-N-(1,1,3-trimethylindan-4-yl)nicotinamide, (2',4'-difluorobiphenyl-2-yl) 3-difluoromethyl-1-methyl-1H-pyrazole-4-carboxamide, (2',4'-dichlorobiphenyl-2-yl) 3-difluoromethyl-1-methyl-1H-pyrazole-4-carboxamide, (2',5'-difluorobiphenyl-2-yl) 3-difluoromethyl-1-methyl-1H-pyrazole-4-carboxamide, (2', 5'-dich lorobiphenyl-2-yl) 3-difluoromethyl-1-methyl-1H-pyrazole-4-carboxamide, (3',5'-difluorobiphenyl-2-yl) 3-difluoromethyl-1-methyl-1H-pyrazole-4-carboxamide, (3',5'-dichlorobiphenyl-2-yl) 3-difluoromethyl-1-methyl-1H-pyrazole-4-carboxamide, (3'-fluorobiphenyl-2-yl) 3-difluoromethyl-1-methyl-1H-pyrazole-4-carboxamide, (3'-chlorobiphenyl-2-yl) 3-difluoromethyl-1-methyl-1H-pyrazole-4-carboxamide, (2'-fluorobiphenyl-2-yl) 3-difluoromethyl-1-methyl-1H-pyrazole-4-carboxamide, (2'-chlorobiphenyl-2-yl) 3-difluoromethyl-1-methyl-1H-pyrazole-4-carboxamide, (3',4',5'-trifluorobiphenyl-2-yl) 3-difluoromethyl-1-methyl-1H-pyrazole-4-carboxamide, (2',4',5'-trifluorobiphenyl-2-yl) 3-difluoromethyl-1-methyl-1H-pyrazole-4-carboxamide, [2-(1,1,2,3,3,3-hexafluoropropoxy)phenyl] 3-difluoromethyl-1-methyl-1H-pyrazole-4-carboxamide, [2-(1,1,2,2-tetrafluoroethoxy)phenyl] 3-difluoromethyl-1-methyl-1H-pyrazole-4-carboxamide, (4'-trifluoromethyithiobiphenyl-2-yl) 3-difluoromethyl-1-methyl-1H-pyrazole-4-carboxamide, N-(3',4'-dichloro-5-fluorobiphenyl-2-yl)-3-difluoromethyl-1-methyl-1H-pyrazole-4-carboxamide, N-(2-(1,3-dimethylbutyl)phenyl)-1,3,3-trimethyl-5-fluoro-1H-pyrazole-4-carboxamide, N-(4'-chloro-3',5'-difluorobiphenyl-2-yl)-3-difluoromethyl-1-methyl-1H-pyrazole-4-carboxamide, N-(4%-chloro-3',5'-difluorobiphenyl-2-yl)-3-trifluoromethyl-1-methyl-1H-pyrazole-4-carboxamide, N-(3',4'-dichloro-5'-fluorobiphenyl-2-yl)-3-trifluoromethyl-1-methyl-1H-pyrazole-4-carboxamide, N-(3',5'-difluoro-4'-methylbiphenyl-2-yl)-3-difluoromethyl-1-methyl-1H-pyrazole-4-carboxamide, N-(3',5'-difluoro-4'-methylbiphenyl-2-yl)-3-trifluoromethyl-1-methyl-1H-pyrazole-4-carboxamide, N-(2-bicyclopropyl-2-ylphenyl)-3-difluoromethyl-1-methyl-1H-pyrazole-4-carboxamide, N-(cis-2-bicyclopropyl-2-ylphenyl)-3-difluoromethyl-1-methyl-1H-pyrazole-4-carboxamide, N-(trans-2-bicyclopropyl-2-ylphenyl)-3-difluoromethyl-1-methyl-1H-pyrazole-4-carboxamide;

carboxylic acid morpholides: dimethomorph, flumorph;

benzamides: flumetover, fluopicolide, fluopyram, zoxamide, N-(3-ethyl-3,5,5-trimethylcyclohexyl)-3-formylamino-2-hydroxybenzamide;

other carboxamides: carpropamid, diciocymet, mandipropamid, oxytetracyclin, silthiofam, N-(6-methoxypyridin-3-yl)cyclopropanecarboxamide;

C) Azoles:
triazoles: azaconazole, bitertanol, bromuconazole, cyproconazole, difenoconazole, diniconazole, diniconazole-M, epoxiconazole, fenbuconazole, fluquinconazole, flusilazol, flutriafol, hexaconazole, imibenconazole, ipconazole, metconazole, myclobutanil, oxpoconazole, paclobutrazol, penconazole, propiconazole, prothioconazole, simeconazole, tebuconazole, tetraconazole, triadimefon, triadimenol, triticonazole, uniconazole, 1-(4-chlorophenyl)-2-([1,2,4]triazol-1-yl)cycloheptanol;

imidazoles: cyazofamid, imazalil, imazalil sulfate, pefurazoate, prochloraz, triflumizole;

benzimidazoles: benomyl, carbendazim, fuberidazole, thiabendazole;

others: ethaboxam, etridiazole, hymexazole, 2-(4-chlorophenyl)-N-[4-(3,4-dimethoxyphenyl)isoxazol-5-yl]-2-prop-2-inyloxyacetamide;

D) Nitrogen-Containing Heterocyclyl Compounds
pyridines: fluazinam, pyrifenox, 3-[5-(4-chlorophenyl)-2,3-dimethylisoxazolidin-3-yl]-pyridine, 3-[5-(4-methylphenyl)-2,3-dimethylisoxazolidin-3-yl]pyridine, 2,3,5,6-tetrachloro-4-methanesulfonylpyridine, 3,4,5-trichloropyridine-2,6-dicarbonitrile, N-(1-(5-bromo-3-chloropyridin-2-yl)ethyl)-2,4-dichloronicotinamide, N-((5-bromo-3-chloropyridin-2-yl)methyl)-2,4-dichloronicotinamide;

pyrimidines: bupirimate, cyprodinil, diflumetorim, fenarimol, ferimzone, mepanipyrim, nitrapyrin, nuarimol, pyrimethanil;

piperazines: triforine;

pyrroles: fludioxonil, fenpiclonil;

morpholines: aldimorph, dodemorph, dodemorph acetate, fenpropimorph, tridemorph;

piperidines: fenpropidin;

dicarboximides: fluorimid, iprodione, procymidone, vinclozolin;

nonaromatic 5-ring heterocycles: famoxadon, fenamidon, octhilinone, probenazole, S-allyl 5-amino-2-isopropyl-3-oxo-4-ortho-tolyl-2,3-dihydropyrazole-1-thiocarboxylate;

others: acibenzolar-S-methyl, amisulbrom, anilazin, blasticidin-S, captafol, captan, quinomethionate, dazomet, debacarb, diclomezine, difenzoquat, difenzoquat methylsulfate, fenoxanil, folpet, oxolinic acid, piperalin, proquinacide, pyroquilon, quinoxyfen, triazoxide, tricyclazole, 2-butoxy-6-iodo-3-propylchromen-4-one, 5-chloro-1-(4,6-dimethoxypyrimidin-2-yl)-2-methyl-1H-benzoimidazole, 5-chloro-7-(4-methylpiperidin-1-yl)-6-(2,4,6-trifluorophenyl)[1,2,4]triazolo[1,5-a]pyrimidine, 6-(3,4-dichlorophenyl)-5-methyl[1,2,4]triazolo[1,5-a]pyrimidin-7-ylamine, 6-(4-tert-butylphenyl)-5-methyl[1,2,4]triazolo[1,5-a]pyrimidin-7-ylamine, 5-methyl-6-(3,5,5-trimethylhexyl)[1,2,4]triazolo[1,5-a]pyrimidin-7-ylamine, 5-methyl-6-octyl[1,2,4]-triazolo[1,5-a]pyrimidin-7-ylamine, 6-methyl-5-octyl[1,2,4]triazolo[1,5-a]pyrimidin-7-ylamine, 6-ethyl-5-octyl[1,2,4]triazolo[1,5-a]pyrimidin-7-ylamine, 5-ethyl-6-octyl[1,2,4]-triazolo[1,5-a]pyrimidin-7-ylamine, 5-ethyl-6-(3,5,5-trimethylhexyl)[1,2,4]triazolo-[1,5-a]pyrimidin-7-ylamine, 6-octy1-5-propyl[1,2,4]triazolo[1,5-a]pyrimidin-7-ylamine, 5-methoxymethyl-6-octyl[1,2,4]triazolo[1,5-a]pyrimidin-7-ylamine, 6-octyl-5-trifluoromethyl[1,2,4]triazolo[1,5-a]pyrimidin-7-ylamine and 5-trifluoromethyl-6-(3,5,5-trimethylhexyl)[1,2,4]triazolo[1,5-a]pyrimidin-7-ylamine;

E) Carbamates and Dithiocarbamates
thio- and dithiocarbamates: ferbam, mancozeb, maneb, metam, methasulphocarb, metiram, propineb, thiram, zineb, ziram;

carbamates: diethofencarb, benthiavalicarb, iprovalicarb, propamocarb, propamocarb hydrochloride, valiphenal, N-(1-(1-(4-cyanophenyl)ethanesulfonyl)but-2-yl)carbamic acid 4-fluorophenyl ester;

F) Other Fungicides
guanidines: dodine, dodine free base, guazatine, guazatine acetate, iminoctadine, iminoctadine triacetate, iminoctadine tris(albesilate);

antibiotics: kasugamycin, kasugamycin hydrochloride hydrate, polyoxins, streptomycin, validamycin A;

nitrophenyl derivatives:
binapacryl, dicloran, dinobuton, dinocap, nitrothalisopropyl, tecnazene;

organometal compounds: fentin salts such as, for example, fentin acetate, fentin chloride, fentin hydroxide;

sulfur-containing heterocyclyl compounds: dithianon, isoprothiolane;

organophosphorus compounds: edifenphos, fosetyl, fosetyl-aluminum, iprobenfos, phosphorous acid and its salts, pyrazophos, toiclofosmethyl;

organochlorine compounds: chlorthalonil, dichlofluanid, dichlorphen, flusulfamide, hexachlorobenzene, pencycuron, pentachlorophenol and its salts, phthalide, quintozene, thiophanate-methyl, tolylfluanid, N-(4-chloro-2-nitrophenyl)-N-ethyl-4-methylbenzenesulfonamide;

inorganic active compounds: phosphorous acid and its salts, Bordeaux mixture, copper salts such as, for example, copper acetate, copper hydroxide, copper oxychloride, basic copper sulfate, sulfur;

others: biphenyl, bronopol, cyflufenamid, cymoxanil, diphenylamin, metrafenon, mildiomycin, oxine-copper, prohexadione-calcium, spiroxamin, tolylfluanid, N-(cyclopropylmethoxyimino(6-difluoromethoxy-2,3-difluorophenyl)methyl)-2-phenylacetamide, N'-(4-(4-chloro-3-trifluoromethylphenoxy)-2,5-dimethylphenyl)-N-ethyl-N-methylformamidine, N'-(4-(4-fluoro-3-trifluoromethylphenoxy)-2,5-dimethylphenyl)-N-ethyl-N-methylformamidine, N'-(2-methyl-5-trifluoromethyl-4-(3-trimethylsilanylpropoxy)phenyl)-N-ethyl-N-methylformamidine, N'-(5-difluoromethyl-2-methyl-4-(3-trimethylsilanylpropoxy)phenyl)-N-ethyl-N-methylformamidine;

G) Growth Regulators abscisic acid, amidochlor, ancymidol, 6-benzylaminopurine, brassinolide, butralin, chlormequat (chlormequat chloride), choline chloride, cyclanilide, daminocide, dikegulac, dimethipin, 2,6-dimethylpyridine, ethephon, flumetralin, flurprimidol, fluthiacet, forchlorfenuron, gibberellic acid, inabenfid, indole-3-acetic acid, maleic hydracide, mefluidid, mepiquat (mepiquat chloride), metconazole, naphthaleneacetic acid, N-6-benzyladenine, paclobutrazole, prohexadione (prohexadione calcium), prohydrojasmone, thidiazuron, triapenthenol, tributyl phosphorotrithioate, 2,3,5-triiodobenzoic acid, trinexapac-ethyl and uniconazole;

the herbicide is selected from:

acetamides: acetochlor, alachlor, butachlor, dimethachlor, dimethenamid, flufenacet, mefenacet, metolachlor, metazachlor, napropamid, naproanilid, pethoxamid, pretilachior, propachlor, thenylchlor;

amino acid analogs: bilanafos, glyphosate, glufosinate, sulfosate;

aryloxyphenoxypropionates: clodinafop, cyhalofop-butyl, fenoxaprop, fluazifop, haloxyfop, metamifop, propaquizafop, quizalofop, quizalofop-P-tefuryl;

bipyridyls: diquat, paraquat;

carbamates and thiocarbamates: asulam, butylate, carbetamide, desmedipham, dimepiperate, eptam (EPTC), esprocarb, molinate, orbencarb, phenmedipham, prosulfocarb, pyributicarb, thiobencarb, tri-allate;

cyclohexanediones: butroxydim, clethodim, cycloxydim, profoxydim, sethoxydim, tepraloxydim, traikoxydim;

dinitroanilines: benfiuralin, ethalfluralin, oryzalin, pendimethalin, prodiamine, trifluralin;

diphenyl ethers: acifluorfen, aclonifen, bifenox, diclofop, ethoxyfen, fomesafen, lactofen, oxyfluorfen;

hydroxybenzonitriles: bromoxynil, dichlobenil, ioxynil;

imidazolinones: imazamethabenz, imazamox, imazapic, imazapyr, imazaquin, imazethapyr;

phenoxyacetic acids: clomeprop, 2,4-dichlorophenoxyacetic acid (2,4-D), 2,4-DB, dichlorprop, MCPA, MCPA-thioethyl, MCPB, mecoprop;

pyrazines: chioridazon, flufenpyr-ethyl, fluthiacet, norflurazon, pyridate;

pyridines: aminopyralid, ciopyralid, diflufenican, dithiopyr, fluridone, fluroxypyr, picloram, picolinafen, thiazopyr;

sulfonylureas: amidosulfuron, azimsulfuron, bensulfuron, chlorimuron-ethyl, chlorsulfuron, cinosulfuron, cyclosulfamuron, ethoxysulfuron, flazasulfuron, flucetosulfuron, flupyrsulfuron, foramsulfuron, halosulfuron, imazosulfuron, iodosulfuron, mesosulfuron, metsulfuron-methyl, nicosulfuron, oxasulfuron, primisulfuron, prosulfuron, pyrazosulfuron, rimsulfuron, sulfometuron, sulfosulfuron, thifensulfuron, triasulfuron, tribenuron, trifloxysulfuron, triflusulfuron, tritosuifuron, 1-((2-chloro-6-propylimidazo[1,2-b]pyridazin-3-yl)sulfonyl)-3-(4,6-dimethoxypyrimidin-2-yl)urea;

triazines: ametryn, atrazine, cyanazine, dimethametryn, ethiozine, hexazinon, metamitron, metribuzin, prometryn, simazine, terbuthylazine, terbutryn, triaziflam;

ureas: chlortoluron, daimuron, diuron, fluometuron, isoproturon, linuron, methabenzthiazuron, tebuthiuron;

other acetolactate synthase inhibitors: bispyribac-sodium, doransulam-methyl, diclosulam, florasulam, flucarbazone, flumetsulam, metosulam, ortho-sulfamuron, penoxsulam, propoxycarbazone, pyribambenz-propyl, pyribenzoxim, pyriftalide, pyriminobac-methyl, pyrimisulfan, pyrithiobac, pyroxasulfone, pyroxsulam;

others: amicarbazone, aminotriazole, anilofos, beflubutamid, benazolin, bencarbazone, benfuresate, benzofenap, bentazone, benzobicyclon, bromacil, bromobutide, butafenacil, butamifos, cafenstrole, carfentrazone, cinidon-ethyl, chlorthal, cinmethylin, clomazone, cumyluron, cyprosulfamide, dicamba, difenzoquat, diflufenzopyr, *Drechslera monoceras*, endothal, ethofumesate, etobenzanid, fentrazamide, flumiclorac-pentyl, flumioxazin, flupoxam, fluorochloridone, flurtamone, indanofan, isoxaben, propanil, propyzamide, quinclorac, quinmerac, mesotrione, methylarsonic acid, naptalam, oxadiargyl, oxadiazon, oxaziclomefone, pentoxazone, pinoxaden, pyraclonil, pyraflufen-ethyl, pyrasulfotol, pyrazoxyfen, pyrazolynate, quinoclamine, saflufenacil, sulcotrion, sulfentrazone, terbacil, tefuryltrione, tembotrione, thiencarbazone, topramezon, 4-hydroxy-3-[2-(2-methoxyethoxymethyl)-6-trifluoromethylpyridine-3-carbonyl]bicyclo[3.2.1]oct-3-en-2-one, (3-[2-chloro-4-fluoro-5-(3-methyl-2,6-dioxo-4-trifluoromethyl-3,6-dihydro-2H-pyrimidin-1-yl)phenoxy]pyridin-2-yloxy) acetic acid ethyl ester, 6-amino-5-chloro-2-cyclopropylpyrimidine-4-carboxylic acid methyl ester, 6-chloro-3-(2-cyclopropyl-6-methylphenoxy)pyridazin-4-ol, 4-amino-3-chloro-6-(4-chlorophenyl)-5-fluoropyridine-2-carboxylic acid, 4-amino-3-chloro-6-(4-chloro-2-fluoro-3-methoxyphenyl)-pyridine-2-carboxylic acid methyl ester, and 4-amino-3-chloro-6-(4-chloro-3-dimethylamino-2-fluorophenyl)pyridine-2-carboxylic acid methyl ester.

The insecticide/nematicide is selected from:

organo(thio)phosphates: acephate, azamethiphos, azinphos-methyl, chlorpyrifos, chlorpyrifos-methyl, chlorfenvinphos, diazinon, dichlorvos, dicrotophos, dimethoate, disulfoton, ethion, fenitrothion, fenthion, isoxathion, malathion, methamidophos, methidathion, methyl-parathion, mevinphos, monocrotophos, oxydemeton-methyl, paraoxon, parathion, phenthoate, phosalone, phosmet, phosphamidon, phorate, phoxim, pirimiphos-methyl, profenofos, prothiofos, sulprophos, tetrachlorvinphos, terbufos, triazophos, trichlorfon;

carbamates: alanycarb, aldicarb, bendiocarb, benfuracarb, carbaryl, carbofuran, carbosulfan, fenoxycarb, furathiocarb, methiocarb, methomyl, oxamyl, pirimicarb, propoxur, thiodicarb, triazamate;

pyrethroids: allethrin, bifenthrin, cyfluthrin, cyhalothrin, cyphenothrin, cypermethrin, alpha-cypermethrin, beta-cypermethrin, zeta-cypermethrin, deltamethrin, esfenvalerate, etofenprox, fenpropathrin, fenvalerate, imiprothrin, lambda-cyha-lothrin, permethrin, prallethrin, pyrethrin I and II, resmethrin, silafluofen, tau-fluvalinat, tefluthrin, tetramethrin, tralomethrin, transfluthrin, profluthrin, dimefluthrin, insect growth inhibitors: a) chitin synthesis inhibitors: benzoylureas: chlorfluazuron, cyromazine, diflubenzuron, flucycloxuron, flufenoxuron, hexaflumuron, lufenuron, novaluron, teflubenzuron, triflumuron; buprofezin, diofenolan, hexythiazox, etoxazole, clofentezine; b) ecdysone antagonists: halofenozide, methoxyfenozide, tebufenozide, azadirachtin; c) juvenoids: pyriproxyfen, methoprene, fenoxycarb; d) lipid biosynthesis inhibitors: spirodiclofen, spiromesifen, spirotetramate;

nicotine receptor agonists/antagonists: clothianidin, dinotefuran, imidacloprid, thiamethoxam, nitenpyram, acetamiprid, thiacloprid, 1-(2-chlorothiazol-5-ylmethyl)-2-nitrimino-3,5-dimethyl[1,3,5]triazinane;

GABA antagonists: endosulfan, ethiprole, fipronil, vaniliprole, pyrafluprole, pyriprole, 5-amino-1-(2,6-dichloro-4-methylphenyl)-4-sulfinamoyl-1H-pyrazole-3-thiocarboxamide;

macrocyclic lactones: abamectin, emamectin, milbemectin, lepimectin, spinosad, spinetoram;

mitochondrial electron transport chain inhibitor (METI) I acaricides: fenazaquin, pyridaben, tebufenpyrad, tolfenpyrad, flufenerim;

METI II and III substances: acequinocyl, fluacrypyrim, hydramethylnon;

decouplers: chlorfenapyr;

inhibitors of oxidative phosphorylation: cyhexatin, diafenthiuron, fenbutatin oxide, propargite;

insect molting inhibitors: cyromazine;

mixed-function oxidase inhibitors: piperonyl butoxide;

sodium channel blockers: indoxacarb, metaflumizone;

others: benclothiaz, bifenazate, cartap, flonicamid, pyridalyl, pymetrozin, sulfur, thiocyclam, flubendiamid, chlorantraniliprole, cyazypyr (HGW86); cyenopyrafen, flupyrazofos, cyfiumetofen, amidoflumet, imicyafos, bistrifluron, and pyrifluquinazon.

In a further preferred embodiment, the crop protection agents are preferably herbicides. In a further preferred embodiment, the crop protection agents are preferably insecticides. In a further preferred embodiment, the crop protection agents are preferably fungicides. In a further preferred embodiment, the fungicides are preferably azoles. In a further preferred embodiment, the azoles are preferably epoxiconazole, fluquinconazole or metconazole.

Further suitable effect substances are additives for foods or animal feed, such as food dyes, amino acids, vitamins, preservatives, antioxidants, fragrances or flavorings.

Examples of auxiliaries for polymers are flame retardants, viscosity improvers or polar liquids, as can be used in the discontinuous phase. Examples of auxiliaries for paper are alkenylsuccinic anhydrides or dialkyldiketenes. Examples of auxiliaries for detergents and cleaners are surfactants or emulsifiers, as can also be used as dispersants in the inverse miniemulsion. Enzymes such as hydrolases or amidases can likewise be used as auxiliaries.

Preferred effect substances are crop protection agents and fertilizers, in particular crop protection agents.

The effect substances can be used in pure form, technical-grade quality, as extract or in a mixture with other effect substances. The effect substances are present in the dispersed phase in dissolved form or in solid form. The total amount of the effect substances is 0.1 to 90% by weight, preferably 5 to 50% by weight, based on the total mixture.

The effect substances can be released from the microcapsules by means of diffusion through the capsule wall or through degradation of the capsule wall. The release rate can be controlled in a targeted manner by internal and external influences which influence the diffusion or the degradation.

Internal influences for controlling the release of the effect substance are, for example, the biodegradability, the chemical, mechanical and physical stability of the microcapsules and the polarity, thickness and uniformity (holes or flaws) of the capsule wall. In addition, according to the invention, compounds may preferably be present inside the capsule or in the capsule wall which influence the release, so-called releasers. Suitable releasers are, for example, enzymes, preferably polyester-hydrolyzing lipases. The enzymes can be the same as those used for the enzyme-catalyzed polymerization of the monomers. Suitable releasers are also acids, bases, free-radical formers or salts for generating an osmotic pressure. Mixtures of releasers are likewise possible.

The total amount of the releaser is generally from 0.01 to 20% by weight, based on the total mixture. The amount is governed by the desired release rate and the prevailing conditions. The person skilled in the art will determine the rate of release of the effect substance by varying the amount under the desired release conditions. External influences for controlling the release of the effect substance are, for example, acidic or basic conditions, microbiological or enzymatic degradation of the capsule wall, mechanical pressure or irradiation, such as UV or electron radiation.

Further additives, for example preservatives, thickeners, release agents or protective colloids and emulsifiers, as can also be used in the process according to the invention are known to the person skilled in the art and are added in the customary amount depending on the desired intended use following production of the microcapsules.

The process according to the invention advantageously takes place in such a way that in each case at least one dispersant, at least one nonpolar liquid, at least one polar liquid, at least one monomer, at least one enzyme catalyzing the polymerization and at least one effect substance are brought together in any desired order and an inverse miniemulsion is produced therefrom. It is likewise possible to prepare premixes. Preferably, at least one enzyme catalyzing the polymerization is introduced into a previously prepared inverse miniemulsion.

The process according to the invention preferably takes place in such a way that at least one dispersant is introduced into at least one part amount of a liquid and one part amount of the monomers. The effect substance and one part amount of the monomers is introduced separately into at least one part amount of the liquid. The two mixtures are brought together and an inverse miniemulsion is produced. Part amounts of the monomers and also the enzyme are then introduced into the miniemulsion. In this connection, "part amount of the monomers" means between 0 and 100% of the total monomers present in the reaction mixture. "At least one part amount" means more than 0% of the amount present in the total mixture.

In one preferred embodiment, one part amount of the monomers is introduced into the miniemulsion, where the part amount is more than 1%, preferably more than 10%.

The process according to the invention generally takes place at a reaction temperature of from 5 to 100° C., often from 20 to 80° C. and frequently from 30 to 65° C. In general, the process takes place at a pressure (absolute values) as a rule from 0.8 to 10 bar, preferably from 0.9 to 2 bar and in particular at 1 bar (atmospheric pressure). The person skilled in the art determines the reaction time according to the desired properties of the microcapsules, for example the degree of polymerization or the thickness of the capsule covering. After the desired reaction time, the enzyme can be destroyed or reused, the microcapsules can be isolated or the reaction mixture can be isolated or further processed in another way.

In general, the solid capsule covering is formed from the monomers during the reaction time in the inverse miniemulsion with catalysis of the enzyme. As a result of the formation of solid capsule coverings, a microcapsule suspension of microcapsules with a solid capsule covering is formed from the miniemulsion.

The releaser can be introduced in any desired process step. If the releaser comprises an enzyme, it is preferably added after the emulsification. Further additives, such as preservatives, can be introduced in any desired process step.

The preparation of the inverse miniemulsion which must be present according to the invention can take place according to the prior art. For this, a macroemulsion is prepared by introducing energy into the mixture of the phases by shaking, beating, stirring, turbulent mixing; by injecting one liquid into another; through oscillation and cavitation in the mixture (e.g. ultrasound); through emulsifying centrifuges; through colloid mills and homogenizers; or by means of a jet nozzle, as described, for example, in WO 2006/053712. The macroemulsion is converted to a miniemulsion with droplet sizes below 1000 nm by homogenization. The homogenization preferably takes place at 0 to 100° C. by using ultrasound, high-pressure homogenizers or other high-energy homogenization apparatuses, such as jet nozzles.

The polymers of the capsule coverings can be postcrosslinked by known processes. Of suitability are usually free-radical processes, for example by free-radical initiators or by UV-initiated crosslinking, or addition processes, for example with diisocyanates or carbodiimides or processes for the transesterification of free OH groups, for example enzymatic transesterification processes or, for example, transesterification of citric acid triesters. The postcrosslinking can take place following completion of the capsule covering or at the same time as producing the capsule covering according to the invention.

The microcapsules produced according to the invention can be provided with a second capsule covering by known processes, for example by organometallically catalyzed, free-radical polymerization, by enzyme-catalyzed polymerization, by polyaddition for producing polyurethane or epoxy resin as second covering, or by polycondensation for producing polyesters or polyamides.

The further use of the capsules is also possible without further work-up. According to the production of the microcapsules according to the invention, they can be isolated as required, i.e. freed from solvents. Suitable methods are, for example, evaporation, spray-drying, freeze-drying, centrifugation, filtration or vacuum drying. In a preferred embodiment, the microcapsules are not isolated following production.

Furthermore, the microcapsules can be converted to dispersions according to the invention by dispersing the microcapsules in water or aqueous solutions, for example by phase transfer processes or flush-analogous transfer processes.

The dispersion comprising microcapsules produced according to the invention or the further worked-up product can be used as component in colorants, cosmetics, pharmaceuticals, crop protection agents, fertilizers, additives for foods or animal feed, auxiliaries for polymers, paper, textile, leather, coatings or detergents and cleaners. It is advantageous that the effect substance can be released again in a targeted manner, in particular in the biosphere where enzymes which degrade polyesters are present ubiquitously.

In a preferred embodiment, the present invention relates to an agrochemical formulation comprising microcapsules according to the invention or microcapsules produced according to the invention.

The agrochemical formulations can comprise further formulation auxiliaries. Within the context of the invention, the expression "formulation auxiliaries" are auxiliaries which are suitable for formulating agrochemical active compounds, such as solvents, carriers, surfactants (ionic or nonionic surfactants, adjuvants, dispersants), preservatives, antifoams and/or antifreezes. Auxiliaries for seed material treatment may optionally also be dyes, binders, gelling agents and/or thickeners.

In general, the agrochemical formulations can comprise 0 to 90% by weight, preferably 1 to 85% by weight, particularly preferably 5 to 80% by weight and in particular 5 to 65% by weight, of formulation auxiliaries.

In a further preferred embodiment, the present invention relates to methods for controlling undesired plant growth, where the undesired plants, the soil on which the undesired plants grow, or their seed materials are treated with an agrochemical formulation according to the invention.

In a further preferred embodiment, the present invention relates to methods for controlling undesired insect or mite infestation on plants and/or for controlling phytopathogenic fungi, where the fungi/insects, their habitat or the plants or soils to be protected from fungal or insect infestation or the plants, the soil on which the plants grow, or their seed materials are treated with an agrochemical formulation according to the invention.

In a further preferred embodiment, the present invention relates to methods for the treatment of seed material with an agrochemical formulation according to the invention and also to seed material treated with an agrochemical formulation according to the invention.

Specifically, the agrochemical formulations according to the invention are suitable for controlling the following plant diseases:

*Albugo* spp. (white rust) in ornamentals, vegetable crops (for example: *A. candida*) and sunflowers (for example *A. tragopogonis*); *Alternaria* spp. (black spot, brown rot) in vegetables, oilseed rape (for example *A. brassicola* or *A. brassicae*), sugarbeet (for example *A. tenuis*), fruit, rice, soybeans and in potatoes (for example *A. solani* or *A. alternata*) and tomatoes (for example *A. solani* or *A. alternata*) and *Alternaria* spp. (leaf blight) on wheat; *Aphanomyces* spp. in sugarbeet and vegetables; *Ascochyta* spp. in cereals and vegetables, for example *A. tritici* (leaf spot) in wheat and *A. hordei* in barley; *Bipolaris* and *Drechslera* spp. (teleomorph: *Cochliobolus* spp.) in maize (for example *D. maydis*), cereals (for example *B. sorokiniana*: common root rot), rice (for example *B. oryzae*) and turf; *Blumeria* (formerly: *Erysiphe*) *graminis* (powdery mildew) in cereals (for example wheat or barley); *Botryosphaeria* spp. (black dead arm disease) in grapevines (for example *B. obtusa*); *Botrytis cinerea* (teleomorph: *Botryotinia fuckeliana*: gray mold) in soft fruit and pome fruit (strawberries, inter alia), vegetables (lettuce, carrots, celery and cabbage, inter alia), oilseed rape, flowers, grapevines, forestry crops and wheat (head rot); *Bremia lactucae* (downy mildew) in lettuce; *Ceratocystis* (syn. *Ophiostoma*) spp. (bluing fungus) in deciduous and coniferous woody species, for example *C. ulmi* (Dutch elm disease) in elms; *Cercospora* spp. (cercospora leaf spot) in maize, rice, sugarbeet (for example *C. beticola*), sugarcane, vegetable, coffee, soybeans (for example *C. sofina* or *C. kikuchii*) and rice; *Cladosporium* spp. in tomatoes (for example *C. fulvum*: leaf mold disease) and cereals, for example *C. herbarum*

(black ear) in wheat; *Claviceps purpurea* (ergot) in cereals; *Colletotrichum* (anamorph: *Helminthosporium* or *Bipolaris*) spp. (leaf spot) in maize (for example *C. carbonum*), cereals (for example *C. sativus*, anamorph: *B. sorokiniana*, common root rot) and rice (for example *C. miyabeanus*, anamorph: *H. oryzae*); *Colletotrichum* (teleomorph: *Glomerella*) spp. (leaf spot, anthracnose) in cotton (for example *C. gossypii*), maize (for example *C. graminicola*: red stalk rot and leaf spot), soft fruit, potatoes (for example *C. coccodes*: foot rot), beans (for example *C. lindemuthianum*) and soybeans (for example *C. truncatum*); *Corticium* spp., for example *C. sasakii* (bordered sheath spot) in rice; *Corynespora cassiicola* (leaf spot) in soybeans and ornamentals; *Cycloconium* spp., for example *C. oleaginum* in olives; *Cylindrocarpon* spp. (for example fruit tree canker or black foot disease, teleomorph: *Nectria* or *Neonectria* spp.) in woody fruiting species, grapevines (for example *C. liriodendri*, teleomorph: *Neonectria liriodendri*, black foot disease) and many woody ornamentals; *Dematophora* (teleomorph: *Rosellinia*) *necatrix* (root/stem rot) in soybeans; *Diaporthe* spp., for example *D. phaseolorum* (soybean stem canker) in soybeans; *Drechslera* (syn. *Helminthosporium*, teleomorph: *Pyrenophora*) spp. in maize, cereals such as barley (for example *D. teres*, net blotch) and in wheat (for example *D. tritici-repentis*: DTR), rice and turf; esca disease (apoplexy) in grapevines, caused by *Formitiporia* (syn. *Phellinus*) *punctata*, *F. mediterranea*, *Phaeomoniella chlamydospora* (formerly *Phaeoacremonium chlamydosporum*), *Phaeoacremonium aleophilum* and/or *Botryosphaeria obtusa*; *Elsinoe* spp. in pome fruit (*E. pyri*) and soft fruit (*E. veneta*: cane spot) and grapevines (*E. ampelina*: grapevine anthracnose); *Entyloma oryzae* (leaf smut) in rice; *Epicoccum* spp. (black ear) in wheat; *Erysiphe* spp. (powdery mildew) in sugarbeet (*E. betae*), vegetables (for example *E. pisi*), such as cucurbits (for example *E. cichoracearum*) and brassicas such as oilseed rape (for example *E. cruciferarum*); *Eutypa lata* (grape canker or grape vine dieback, anamorph: *Cytosporina lata*, syn. *Libertella blepharis*) in woody fruiting species, grapevines and many woody ornamentals; *Exserohilium* (syn. *Helminthosporium*) spp. in maize (for example *E. turcicum*); *Fusarium* (teleomorph: *Gibberella*) spp. (wilt, foot rot and culm rot) in various plants such as, for example *F. graminearum* or *F. culmorum* (foot rot, partial ear sterility) in cereals (for example wheat or barley), *F. oxysporum* in tomatoes, *F. solani* on soybeans and *F. verticilliodes* in maize; *Gaeumannomyces graminis* (take-all) in cereals (for example wheat or barley) and maize; *Gibberella* spp. in cereals (for example *G. zeae*) and rice (for example *G. fujikoroi*: bakanae disease); *Glomerella cingulata* in grapevines, pome fruit and other plants and *G. gossypii* in cotton; grain staining complex in rice; *Guignardia bidwellii* (black rot) in grapevines; *Gymnosporangium* spp. in Rosaceae and juniper, for example *G. sabinae* (pear rust) in pears; *Helminthosporium* spp. (syn. *Drechslera*, teleomorph: *Cochliobolus*) in maize, cereals and rice; *Hemileia* spp., for example *H. vastatrix* (coffee leaf rust) in coffee; *Isariopsis clavispora* (syn. *Cladosporium vitis*) in grapevines; *Macrophomina phaseolina* (syn. *phaseoli*) (root rot/charcoal rot) in soybeans and cotton; *Microdochlium* (syn. *Fusarium*) *nivale* (snow mold) in cereals (for example wheat or barley); *Microsphaera diffusa* (powdery mildew) in soybeans; *Monilinia* spp., for example *M. laxa*, *M. fructicola* and *M. fructigena* (blossom blight and spur canker) in stone fruit and other Rosaceae; *Mycosphaerella* spp. in cereals, bananas, soft fruit and peanuts such as, for example, *M. graminicola* (anamorph: *Septoria tritici*, septoria leaf blotch) in wheat or *M. fijiensis* (black Sigatoka disease) in bananas; *Peronospora* spp. (downy mildew) in cabbage (for example *P. brassicae*), oilseed rape (for example *P. parasitica*), alliums (for example *P. destructor*), tobacco (*P. tabacina*) and soybeans (for example *P. manshurica*); *Phakopsora pachyrhizi* and *P. meibomiae* (soybean rust) in soybeans; *Phialophora* spp. for example in grapevines (for example *P. tracheiphlla* and *P. tetraspora*) and soybeans (for example *P. gregata*: brown stem rot); *Phoma lingam* (phoma stern canker) in oilseed rape and cabbage and *P. betae* (leaf spot) in sugarbeet; *Phomopsis* spp. in sunflowers, grapevines (for example *P. viticola*: phomopsis cane and leaf spot) and soybeans (for example stem canker: *P. phaseoli*, teleomorph: *Diaporthe phaseolorum*); *Physoderma maydis* (brown spot) in maize; *Phytophthora* spp. (wilt, root rot, leaf rot, stem rot and fruit rot) in a variety of plants such as in bell pepper and cucurbits (for example *P. capsici*), soybeans (for example *P. megasperma*, syn. *P. sojae*), potatoes and tomatoes (for example *P. infestans*: late blight) and deciduous woody species (for example *P. ramorum*: sudden oak death); *Plasmodiophora brassicae* (clubroot disease) in cabbage, oilseed rape, radish and other plants; *Plasmopara* spp., for example *P. viticola* (downy mildew) in grapevines and *P. halstedii* in sunflowers; *Podosphaera* spp. (powdery mildew) in Rosaceae, hops, pome fruit and soft fruit, for example *P. leucotricha* in apple; *Polymyxa* spp., for example in cereals such as barley and wheat (*P. graminis*) and sugarbeet (*P. betae*), and the virus diseases transmitted thereby; *Pseudocercosporella herpotrichoides* (eyespot, teleomorph: *Tapesia yallundae*) in cereals, for example wheat or barley; *Pseudoperonospora* (downy mildew) in a variety of plants, for example *P. cubensis* in cucurbits or *P. humuli* in hops; *Pseudopezicula tracheiphlla* (red fire disease, anamorph: *Phialophora*) in grapevines; *Puccinia* spp. (rust) in a variety of plants, for example *P. triticina* (leaf rust of wheat), *P. striiformis* (yellow rust), *P. hordei* (brown rust), *P. graminis* (stem rust) or *P. recondita* (brown leaf rust of rye) in cereals such as, for example, wheat, barley or rye, and in asparagus (for example *P. asparagi*); *Pyrenophora* (anamorph: *Drechslera*) *tritici-repentis* (tan spot) in wheat or *P. teres* (net blotch) in barley; *Pyricularia* spp., for example *P. oryzae* (teleomorph: *Magnaporthe grisea*, rice blast) in rice and *P. grisea* in turf and cereals; *Pythium* spp. (damping-off) in turf, rice, maize, wheat, cotton, oilseed rape, sunflowers, sugarbeet, vegetables and other plants (for example *P. ultimum* or *P. aphanidermatum*); *Ramularia* spp., for example *R. collo-cygni* (ramularia leaf spot/physiological leaf spots) in barley and *R. beticola* in sugarbeet; *Rhizoctonia* spp. in cotton, rice, potatoes, turf, maize, oilseed rape, sugarbeet, vegetables and a variety of other plants, for example *R. solani* (rhizoctonia root/stem rot) in soybeans, *R. solani* (bordered sheath spot) in rice or *R. cerealis* (sharp eyespot) in wheat or barley; *Rhizopus stolonifer* (black bread mold) in strawberries, carrots, cabbage, grapevines and tomatoes; *Rhynchosporium secalis* (leaf spot) in barley, rye and triticale; *Sarocladium oryzae* and *S. attenuatum* (sheath rot) in rice; *Sclerotinia* spp. (stem rot, sclerotinia disease) in vegetable crops and arable crops such as oilseed rape, sunflowers (for example *Sclerotinia sclerotiorum*) and soybeans (for example *S. rolfsii*); *Septoria* spp. in a variety of plants, for example *S. glycines* (septoria blight) in soybeans, *S. tritici* (Septoria tritici blotch) in wheat and *S.* (syn. *Stagonospora*) *nodorum* (*Stagonospora nodorum* leaf and glume blotch) in cereals; *Uncinula* (syn. *Erysiphe*) necator (powdery mildew, anamorph: *Oidium tuckerr*) in grapevines; *Setospaeria* spp. (maize leaf blight) in maize (for example *S. turcicum*, syn. *Helminthosporium turcicum*) and turf; *Sphacelotheca* spp. in maize, (for example *S. reillana*: head smut), millet/sorghum and sugarcane; *Sphaerotheca fuliginea* (powdery mildew) in cucurbits; *Spongospora subterranea* (powdery scab) in potatoes and the virus diseases transmitted thereby; *Stagonospora* spp. in cereals, for example *S. nodorum* (*Stagonospora nodorum* leaf and glume blotch, teleomorph: *Leptosphaeria* [syn. *Phaeosphaeria*] *nodorum*) in wheat; *Synchytrium endobioticum* in potatoes (potato wart disease); *Taphrina* spp., for example *T. deformans* (leaf curl) in peach and *T. pruni* (plum pocket disease) in plums; *Thielaviopsis* spp. (black root rot) in tobacco, pome fruit, vegetable crops, soybeans and cotton, for example *T. basicola* (syn. *Chalara elegans*); *Tilletia* spp. (stinking smut or smooth-spored bunt) in cereals such as, for example, *T. tritici* (syn. *T. caries*, wheat bunt) and *T. controversa* (dwarf bunt) in wheat; *Typhula incarnata* (snow blight) in barley or wheat; *Urocystis* spp., for example *U. occulta* (stalk smut) in rye; *Uromyces* spp. (rust) in vegetable plants such as beans (for example *U. appendiculatus*, syn. *U. phaseoli*) and sugarbeet (for example *U. betae*); *Ustilago* spp. (loose smut) in cereals (for example *U. nuda* and *U. avaenae*), maize (for example *U. maydis*: maize blister smut) and sugarcane; *Venturia* spp. (scab) in apples (for example *V. inaequalis*) and pears; and *Verticillium* spp. (verticillium wilt, tip rot) in a variety of plants such as woody fruiting and ornamental species, grapevines, soft fruit, vegetable crops and arable crops such as, for example, *V. dahliae* in strawberries, oilseed rape, potatoes and tomatoes.

Moreover, the agrochemical formulations according to the invention are suitable for controlling harmful fungi in the protection of materials and buildings (for example timber, paper, dispersions for painting, fibers or wovens) and in the protection of stored products. Harmful fungi which are of particular importance in the protection of timber and buildings are: Ascomycetes such as *Ophiostoma* spp., *Ceratocystis* spp., *Aureobasidium pullulans*, *Scierophoma* spp., *Chaetomium* spp., *Humicola* spp., *Petriella* spp., *Trichurus* spp.; Basidiomycetes such as *Coniophora* spp., *Coriolus* spp., *Gloeophyllum* spp., *Lentinus* spp., *Pleurotus* spp., *Poria* spp., *Serpula* spp. and *Tyromyces* spp., Deuteromycetes such as *Aspergillus* spp., *Cladosporium* spp., *Penialium* spp., *Trichoderma* spp., *Alternaria* spp., *Paecilomyces* spp. and Zygomycetes such as *Mucor* spp., and moreover, in the protection of materials, the following yeasts: *Candida* spp. and *Saccharomyces cerevisae*.

Moreover, the agrochemical formulations according to the invention are suitable for controlling undesired plant growth. Controlling undesired plant growth is understood as meaning the destruction of weeds. Weeds are understood in the widest sense as all those plants which grow in places where they are undesired, such as, for example:

Dicotyledonous weeds of the genus: *Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus, Taraxacum.*

Monocotyledonous weeds of the genus: *Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristyslis, Sagittaria, Eleocharis, Scirpus, Paspalum, Ischaemum, Sphenoclea, Dactyloctenium, Agrostis, Alopecurus, Apera.*

Overall, the process according to the invention offers many advantages over conventional processes for producing microcapsules: low reaction temperatures and largely neutral pH values permit the encapsulation of temperature- and pH-sensitive effect substances; the polymers for the capsule covering can be directly produced in situ without expensive storage being required; the polymer is produced by the enzyme at low temperatures and not by energy-intensive, classic polymerization processes which mostly demand completely anhydrous conditions; the polymerization catalyst is very readily biocompatible and can be reused, in contrast to organometallic polymerization catalysts.

The microcapsules produced according to the invention and also the dispersions comprising microcapsules likewise offer advantages: the capsule covering of the microcapsules is thicker than in other production processes, it can be varied in thickness more easily or be provided with an additional capsule covering, it can, if required, be degraded again in a targeted manner in order to release the effect substances. The capsule core of the microcapsules can comprise effect substances which are thermally labile or sensitive in some other way, it can also comprise effect substances dissolved in polar liquid. A further advantage of the dispersions is that they can be obtained directly from the production process.

The examples below explain the invention without limiting it.

EXAMPLES

Feed Materials

The nonpolar phase used was a partially hydrogenated mineral oil distillate with boiling point from 260 to 280° C., for example Isopar® from Exxon Mobil Chemical, or a paraffin oil (white, CAS 8012-95-1).

The enzyme used for the polymerization of the monomers was an immobilized lipase from Candida antarctica type B, for example an enzyme which is a lipase from Candida antarctica type B immobilized on spherical polymer beads, available from Novozymes, Denmark.

The dispersant A used was a mixture of emulsifiers which comprises ethoxylated fatty alcohols and sorbitan fatty acid esters, for example 51.72% by weight of Arlacel® P134 (polyethylene glycol-30 dipolyhydroxystearate, Uniqema), 34.48% by weight of Span® 85 (sorbitan trioleate, Uniqema) and 6.90% by weight of Cremophor® A6 (ceteareth-6 and stearyl alcohol, BASF) and 6.9% by weight of Span® 80 (sorbitan monooleate, Uniqema), where the % by weight are based on the total amount of dispersants.

The dispersant B used was a polyester-polyethylene oxide-polyester block copolymer with a molar mass of >1000 g/mol which is prepared by reacting condensed 12-hydroxystearic acid with polyethylene oxide according to the teaching of EP 0 000 424 B1 (Hypermer® B-246, Croda).

The dispersant C used was a polyethylene glycol sorbitan monooleate with a degree of ethoxylation of 20 (Tween® 80).

The monomer used was c-caprolactone for producing the polymer-containing capsule covering, for example from Fluka with a content of >99%.

The effect substance used was a fungicidal crop protection agent, for example triticonazole. Alternatively, a colorant, for example Basacid® Blue 756 (C.I. Acid Blue 9, triphenylmethane dye, for example available from BASF SE) was used as effect substance. Basacid Blue 756 is insoluble in Isopar® V, whereas it dissolves in propylene carbonate and in caprolactone. As further alternatives, propylene carbonate was used as effect substance.

For the staining for the light microscopy, the dye Sudan® Blue (anthraquinone dye, C.I. Solvent Blue 79, available, for example, from BASF SE) was used. It dissolves only in very hydrophobic media, such as in Isopar® V and polycaprolactone. However, it is poorly soluble in water or propylene carbonate.

Example 1

Figure 1:
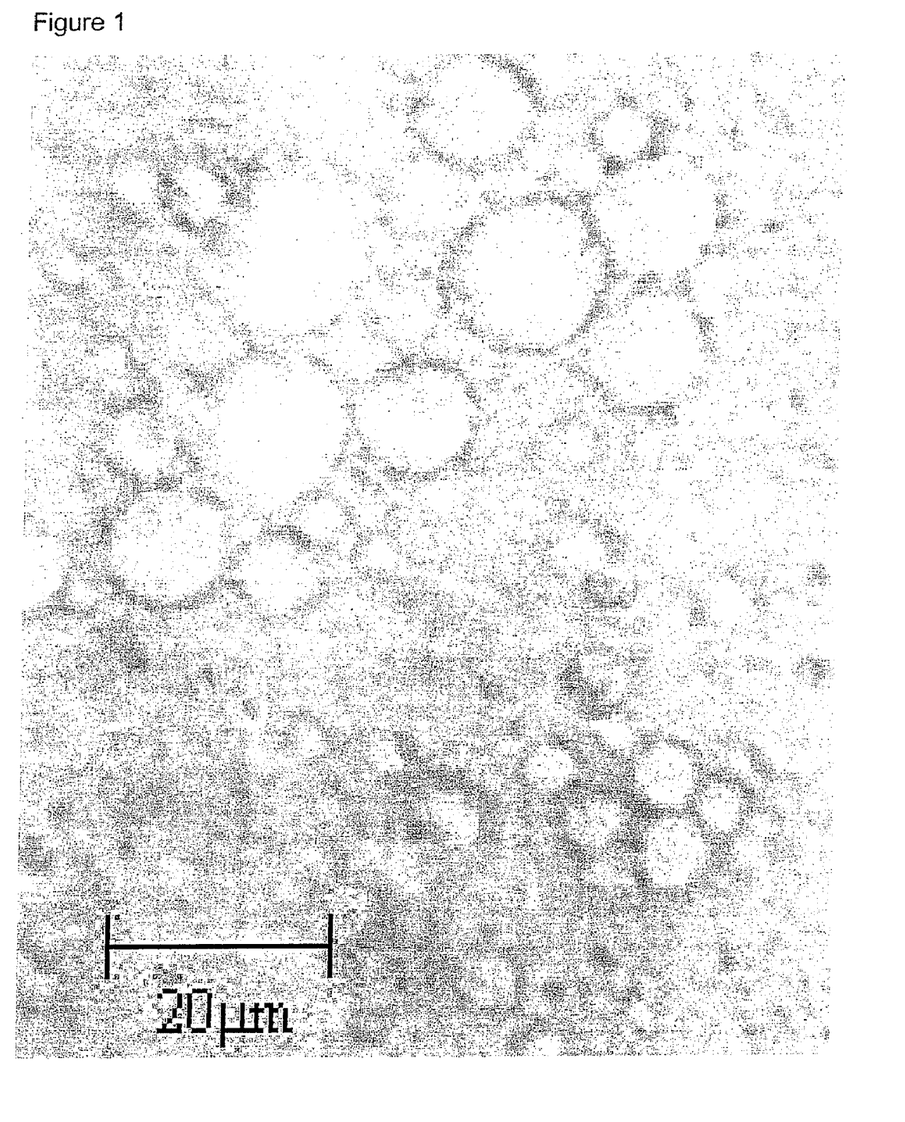
FIG. 1 shows microcapsules with a particle diameter of 5 to 20 microns in which the capsule covering and the nonpolar phase were dyed with Sudan Blue.

The following amounts were used for the preparation of 80.0 g of inverse miniemulsion:
38.00 g of partially hydrogenated mineral oil distillate
2.00 g of dispersant A
0.80 g of ε-caprolactone
39.20 g of propylene carbonate
0-10 μl of water The dispersant was weighed into the sample vessel and dissolved in the partially hydrogenated mineral oil distillate. The caprolactone and propylene carbonate were added to the oil phase with vigorous stirring by means of a magnetic stirrer, then the water was added and the mixture was preemulsified. Using an ultrasound processor UP 400S from Hielscher, an inverse miniemulsion was prepared therefrom with ice cooling (5 min, 100%, Sonotrode H7). Using a light microscope (1000× magnification), the drop size distribution of the miniemulsion was determined as 200-1000 nm. After the ultrasound emulsification, 20 mg of enzyme were added to each mixture and the miniemulsion was polymerized at 40° C. for 24 hours. The microcapsules had a particle diameter of 5 to 20 μm (see FIG. 1; for clarification, the capsule covering and the nonpolar phase were dyed with Sudan Blue).
Water addition
Mixture A) 0 μl of water
Mixture B) 1 μl of water
Mixture C) 2 μl of water
Mixture D) 10 μl of water Example 2

Figure 2:
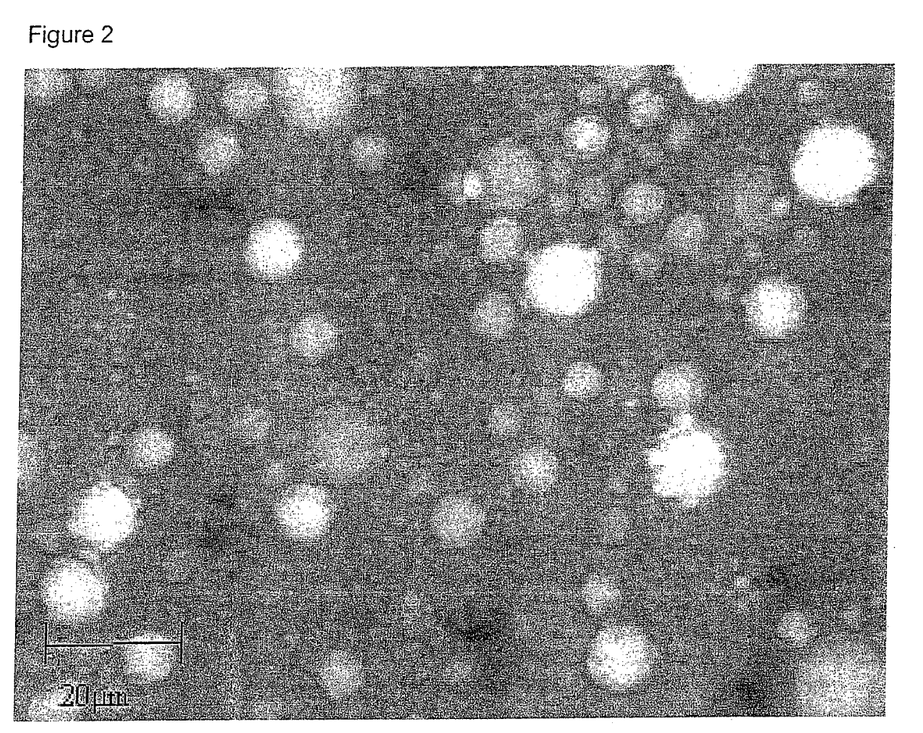
FIG. 2 shows capsules with polycaprolactone covering in a continuous phase of partially hydrogenated mineral oil distillate which has been dyed with Sudan Blue.

The following amounts were used for the preparation of 20.0 g of inverse miniemulsion:
9.50 g of partially hydrogenated mineral oil distillate
0.50 g of dispersant A
0.20 g of ε-caprolactone
9.80 g of propylene carbonate
2 μl of water The dispersant was weighed into the sample vessel and dissolved in the partially hydrogenated mineral oil distillate. The propylene carbonate was added to the oil phase with vigorous stirring using a magnetic stirrer, then the water was added and the mixture was preemulsified. Using an ultrasound processor UP 400S from Hielscher, an inverse miniemulsion was produced therefrom with ice cooling (5 min, 100%, Sonotrode H7). Using a light microscope (1000× magnification), the drop size distribution of the miniemulsion was determined as 200-1000 nm. Following the ultrasound emulsification, the caprolactone was added to the mixture and carefully stirred in. 20 mg of enzyme were added and the miniemulsion is polymerized at 40° C., for 24 hours. The microcapsules had a particle diameter of from 5 to 20 μm. FIG. 2 shows capsules with polycaprolactone covering in a continuous phase of partially hydrogenated mineral oil distillate which has been dyed with Sudan Blue. Individual bulk particles of polycaprolactone were also dyed blue by Sudan Blue.

Example 3

Figure 3:
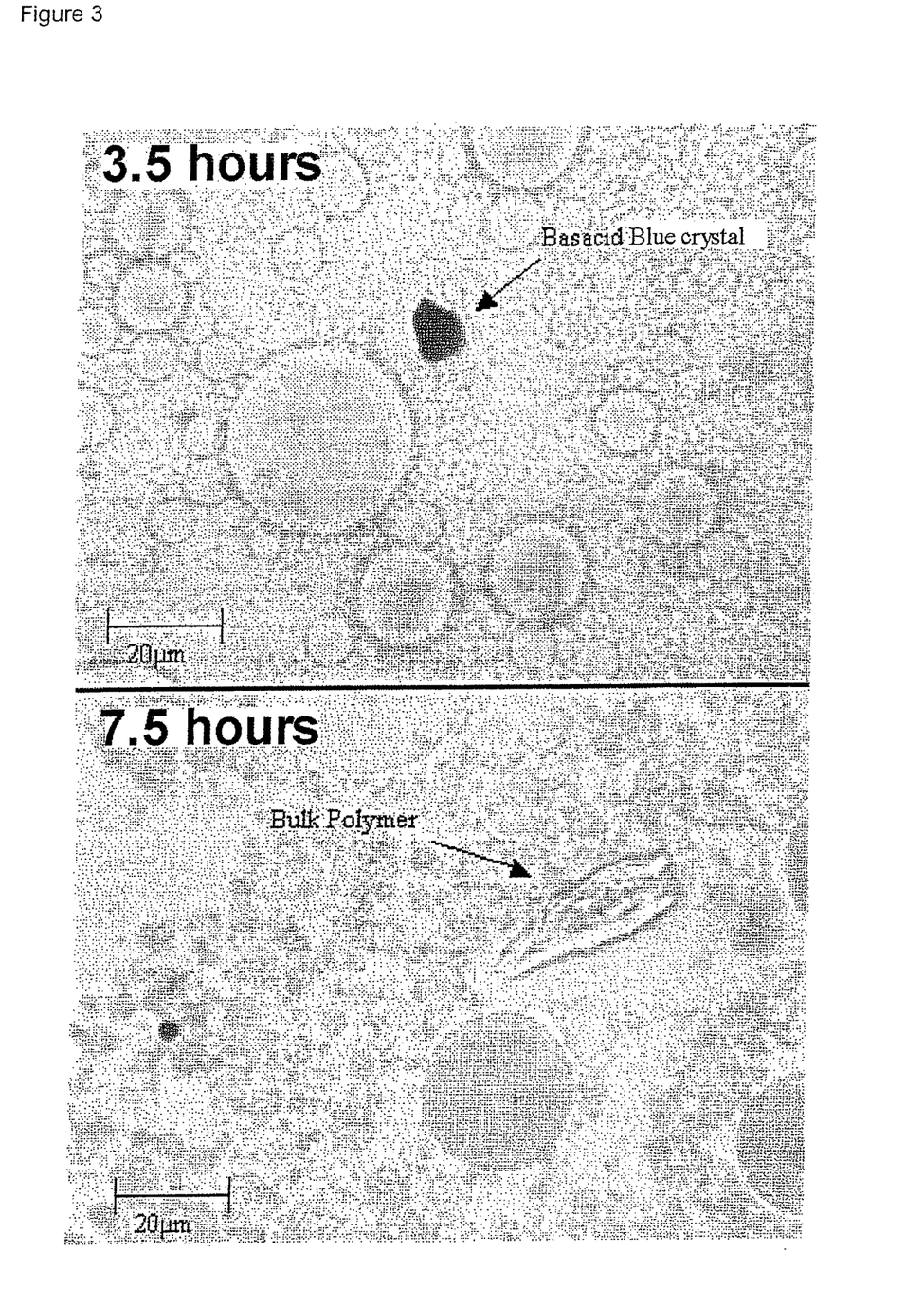
FIG. 3 shows microcapsules whose capsule core has been dyed by the effect substance Basacid Blue.

The following amounts were used for the preparation of 20.0 g of inverse miniemulsion:
9.50 g of partially hydrogenated mineral oil distillate
0.50 g of dispersant A
0.20 g of ε-caprolactone
9.80 g of propylene carbonate
50 mg of Basacid Blue 756
2 μl of water The dispersant was weighed into the sample vessel and dissolved in the partially hydrogenated mineral oil distillate. The Basacid Blue was dissolved in the propylene carbonate with stirring using a magnetic stirrer, then the water was added. The propylene carbonate phase was added to the oil phase and preemulsified. Using an ultrasound processor UP 400S from Hielscher, an inverse miniemulsion was prepared therefrom with ice cooling (5 min, 100%, Sonotrode H7). Using a light microscope (1000× magnification), the drop size distribution of the miniemulsion was determined as 200-1000 nm. Following the ultrasound emulsification, 20 mg of enzyme were added and the miniemulsion is polymerized at 40° C. for 24 hours. The microcapsules had a particle diameter of from 5 to 20 μm. FIG. 3 shows microcapsules whose capsule core has been dyed by the effect substance Basacid Blue. The continuous phase is colorless. Moreover, an undissolved Basacid Blue crystal about 10 μm in size can be seen and a particle of polycaprolactone about 30 μm in length.

Example 4

The following amounts were used for the preparation of 20.0 g of inverse miniemulsion:
9.50 g of partially hydrogenated mineral oil distillate
0.50 g of dispersant A
1.0 g of ε-caprolactone
8.55 g of propylene carbonate
0.45 g of triticonazole The dispersant was weighed into the sample vessel and dissolved in the partially hydrogenated mineral oil distillate. The effect substance triticonazole was dissolved in propylene carbonate and caprolactone. The propylene carbonate phase was added to the oil phase and preemulsified. Using an ultrasound processor UP 400S from Hielscher, an inverse miniemulsion was prepared therefrom with ice cooling (5 min, 100%, Sonotrode H7).

Following the ultrasound emulsification, 100 mg of enzyme were added and the miniemulsion was stirred at 60° C. for 24 hours.

After the polymerization, a sample was diluted with paraffin oil and dyed with Sudan Blue. Under the microscope at 400× magnification, microcapsules (including burst ones) could be seen clearly. The microcapsules have a particle diameter of from <1 μm to 10 μm. Bulk polymer could not be identified. By adding water, it was possible to convert the microcapsules to the aqueous phase.

Example 5

The following amounts were used for the preparation of an inverse miniemulsion:
22.8 g of partially hydrogenated mineral oil distillate
6.0 g of ε-caprolactone
19.2 mg of D-sorbitol
329 mg of triticonazole
1.20 g of dispersant B The dispersant was initially introduced in a sample vessel and dissolved in partially hydrogenated mineral oil distillate with stirring. In a further vessel, triticonazole was dissolved in a mixture of caprolactone and sorbitol. The homogeneous solutions were then mixed together and preemulsified by stirring with a magnetic stirrer (60 min at room temperature). By means of ultrasound (ultrasound processor UP 400S from Hielscher), an inverse miniemulsion was prepared therefrom with cooling by means of an ice bath (5 min, 100% with Sonotrode H7) and, following the addition of 100 mg of enzyme, polymerized for 48 h at 60° C. Electron micrographs show the resulting spherical particles with particle sizes of 1-10 μm.

Example 6

The following amounts were used for the preparation of an inverse miniemulsion:
45.60 g of paraffin oil
11.34 g of ε-caprolactone
18.3 mg of glycerol
60 mg of dispersant C
658 mg of triticonazole
2.40 g of dispersant B The dispersants were initially introduced in a sample vessel and dissolved in paraffin oil with stirring. In a further vessel, triticonazole and glycerol were dissolved in caprolactone. The homogeneous solutions were then mixed together and preemulsified by stirring with a magnetic stirrer for 60 min at room temperature. By means of ultrasound (ultrasound processor UP 400S from Hielscher), an inverse miniemulsion was prepared therefrom with cooling by means of an ice bath (5 min, 100% with Sonotrode H7) and, following the addition of 100 mg of enzyme, polymerized for 48 h at 60° C. Electron-microscopic investigations reveal spherical particles with sizes of 1-10 μm.

Example 7

The following amounts were used for the preparation of the inverse miniemulsion:
120 g of partially hydrogenated mineral oil distillate
24.0 g of propylene carbonate
6.0 g of ε-caprolactone
19.2 mg of D-sorbitol
1.65 g of triticonazole
3.0 g of dispersant B The dispersant was initially introduced in a sample vessel and dissolved in partially hydrogenated mineral oil distillate with stirring. In a further vessel, triticonazole and D-sorbitol were dissolved in a mixture of caprolactone and propylene carbonate. The homogeneous solutions were then mixed together and preemulsified by stirring with a magnetic stirrer for 60 min at room temperature. By means of ultrasound (ultrasound processor UP 400S from Hielscher), an inverse miniemulsion was prepared therefrom with cooling by means of an ice bath (5 min, 100% with Sonotrode H7) and, following the addition of 100 mg of enzyme, polymerized for 48 h at 60° C. On photo micrographs (1000× magnification), the resulting capsules exhibited particle sizes of 1-10 μm.

The invention claimed is:

1. A process for producing microcapsules comprising a capsule core comprising an effect substance and a polymer-containing capsule covering, said method comprising forming a capsule covering by treating $C_2$-$C_{18}$ lactones which are present in an inverse miniemulsion comprising a continuous non-polar phase and a discontinuous polar phase, with an enzyme effective to catalyze polymerization of the lactones, wherein:
    said polar phase comprises a polar liquid and said non-polar phase comprises a non-polar liquid;
    said polar liquid comprises less than 5 wt. % water;
    said effect substance is present in solid, dissolved, emulsified or dispersed form in a discontinuous polar phase; and
    said enzyme comprises a hydrolase.

2. A process for producing microcapsules comprising a capsule core comprising an effect substance and a polymer containing capsule covering, said process comprising forming a capsule covering by treating C2-C18 lactones which are present in an inverse miniemulsion comprising a continuous non-polar phase and a discontinuous polar phase, with an enzyme effective to catalyze polymerization of the lactones, wherein:
    said polar phase comprises a polar liquid and said non-polar phase comprises a non-polar liquid;
    said polar liquid comprises less than 5 wt. % water;
    said effect substance is present in solid, dissolved, emulsified, or dispersed form in a discontinuous polar phase; and
    said enzyme comprises a hydrolase;
    wherein said enzyme comprises an oxidoreductase.

3. The process of claim 1, wherein said effect substance is a colorant, cosmetic, pharmaceutical, crop protection agent, fertilizer, or an additive for foods or animal feed.

4. The process of claim 1, wherein said effect substance is a crop protection agent or a fertilizer.

5. A microcapsule obtainable by means of the process of claim 1.

6. A dispersion comprising said microcapsules of claim 5.

7. An agrochemical formulation comprising microcapsules of claim 5.

8. The process of claim 1, further comprising a releaser is present in the capsule covering.

9. The process of claim 8, wherein said releaser comprises at least one enzyme.

10. The process of claim 1, further comprising a releaser is present in the capsule core.

11. The process of claim 10, wherein said releaser comprises at least one enzyme.

* * * * *